(12) United States Patent
Law et al.

(10) Patent No.: US 9,895,462 B2
(45) Date of Patent: Feb. 20, 2018

(54) METHOD AND APPARATUS FOR HIGH EFFICIENCY AIR PURIFICATION

(75) Inventors: Sui Chun Law, Hong Kong (CN); Yiu Wai Chan, Hong Kong (CN)

(73) Assignee: Sui Chun Law, Fo Tan, N.T (HK)

( * ) Notice: Subject to any disclaimer, the term of this patent is extended or adjusted under 35 U.S.C. 154(b) by 515 days.

(21) Appl. No.: 14/118,951

(22) PCT Filed: May 18, 2012

(86) PCT No.: PCT/CN2012/075757
§ 371 (c)(1),
(2), (4) Date: Nov. 20, 2013

(87) PCT Pub. No.: WO2012/159554
PCT Pub. Date: Nov. 29, 2012

(65) Prior Publication Data
US 2015/0297771 A1    Oct. 22, 2015

(30) Foreign Application Priority Data

May 20, 2011    (CN) .......................... 2011 1 0148952

(51) Int. Cl.
*A61L 9/00*    (2006.01)
*B01D 53/04*    (2006.01)
(Continued)

(52) U.S. Cl.
CPC .............. *A61L 9/00* (2013.01); *B01D 53/04* (2013.01); *B01D 53/885* (2013.01); *F24F 13/28* (2013.01);
(Continued)

(58) Field of Classification Search
CPC ......... A61L 9/00; B01D 53/04; B01D 53/885; B01D 2257/90; B01D 2257/708;
(Continued)

(56) References Cited

U.S. PATENT DOCUMENTS

| 726,564 A | * | 4/1903 | Peirce | .................. | B01D 29/035 |
| | | | | | 210/162 |
| 5,085,771 A | * | 2/1992 | Huang | ................. | B01D 29/071 |
| | | | | | 209/205 |

(Continued)

FOREIGN PATENT DOCUMENTS

| CN | 1712826 A | 12/2005 |
| CN | 101469897 A | 7/2009 |

(Continued)

*Primary Examiner* — Amber R Orlando
*Assistant Examiner* — Britanny Precht
(74) *Attorney, Agent, or Firm* — Rosenberg, Klein & Lee

(57) ABSTRACT

The present invention discloses an air purification apparatus. The air purification apparatus comprising: a casing which contains at least one apparatus air inlet and at least one apparatus air outlet; at least one main filter which is being installed at the apparatus air inlet and/or within the casing; at the periphery of the main filter, there locates a primary air flow inlet and a secondary air flow inlet. When a primary air flow is drawn to flow from the upstream to the downstream positions inside the casing, the primary air flow is adapted to pass by at least one edge of the exterior of the main filter, resulting at least two exterior surfaces of the main filter being exerted with different atmospheric pressures. Through the secondary air flow inlet, a secondary air flow is entrained through the main filter and flows from its exterior surface is exerted with higher atmospheric pressure to its exterior surface is exerted with lower atmospheric pressure. The invention offers an air purification apparatus which owns the characteristics of simple structure, able to extend the lifespan of the filter cost effectively, low energy consumption and induced low noise level.

14 Claims, 13 Drawing Sheets

(51) Int. Cl.
*B01D 53/88* (2006.01)
*F24F 13/28* (2006.01)

(52) U.S. Cl.
CPC .. *B01D 2253/102* (2013.01); *B01D 2253/108* (2013.01); *B01D 2255/802* (2013.01); *B01D 2257/708* (2013.01); *B01D 2257/90* (2013.01); *B01D 2258/06* (2013.01)

(58) Field of Classification Search
CPC ........ B01D 2253/102; B01D 2255/802; B01D 2258/06; B01D 2253/108; F24F 13/28
See application file for complete search history.

(56) References Cited

U.S. PATENT DOCUMENTS

| 6,391,090 | B1 | 5/2002 | Alvarez, Jr. et al. |
| 6,923,851 | B1 * | 8/2005 | Butler ................ B01D 46/0023 55/324 |
| 2005/0284114 | A1 | 12/2005 | Kim et al. |
| 2009/0162255 | A1 | 6/2009 | Chan et al. |

FOREIGN PATENT DOCUMENTS

| JP | 2005-13789 A | 1/2005 |
| JP | 2009-186058 A | 8/2009 |

* cited by examiner

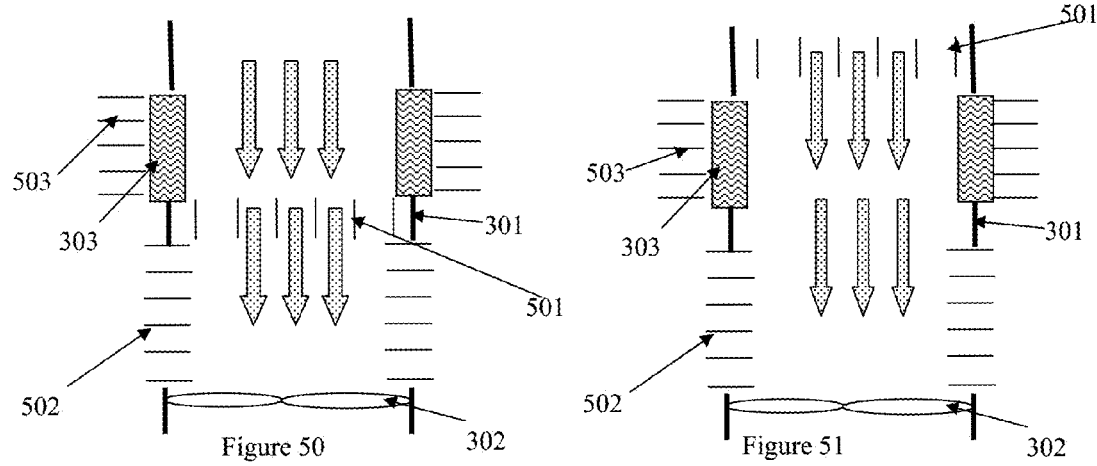
Figure 50  Figure 51
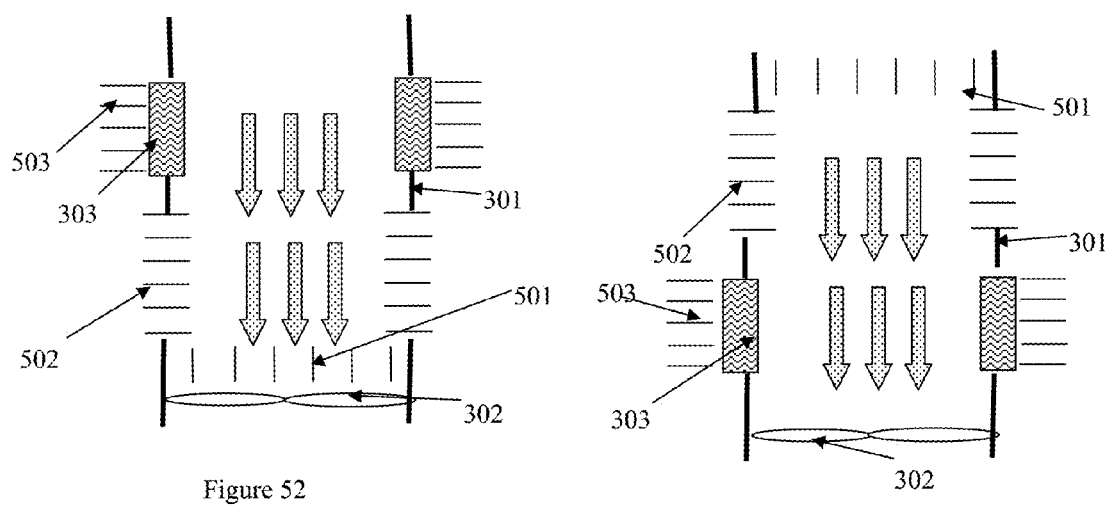
Figure 52
Figure 53
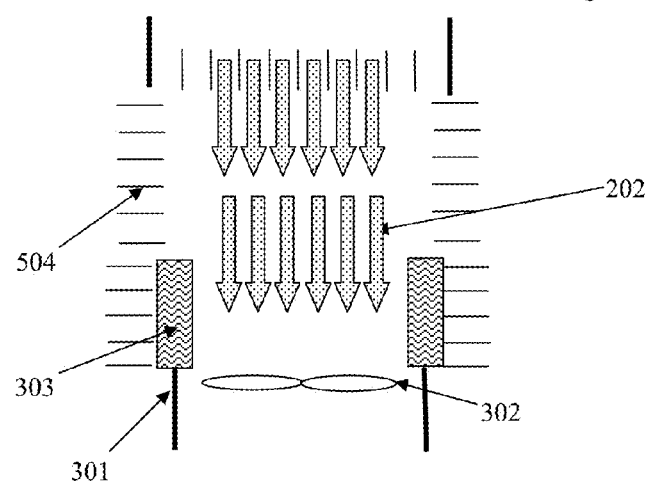
Figure 54

METHOD AND APPARATUS FOR HIGH EFFICIENCY AIR PURIFICATION

FIELD OF THE INVENTION

The present invention patent is relating to the field of environmental protection, and more specifically, it is related to an apparatus for air purification.

BACKGROUND OF THE INVENTION

The air pollutants exist in two major physical phases: the particle phase pollutants are pollutants with significant physical sizes including dust particles, airborne bacteria and mold, they may be composed and be bound together by different matters with different compositions, with sizes range from ¹/₁₀₀ micron to a few hundred micron; the gaseous phase pollutants are pollutants with simple chemical structures, the size of the gaseous phase pollutants are small from angstrom to nano-scale. Odor molecules and volatile organic compounds are examples of gaseous phase pollutants.

To deal with these two types of pollutants, different techniques of purification methods are generally employed. Filtration is one of the conventional purification methods. High efficiency particulate air filter (HEPA Filter) may be employed to remove the pollutants from the air. Other method such as generating high voltage by electrostatic precipitator or by emitting negative ions, which further charges up the suspended particulates and dust matters in the air, and collection the negatively charged suspended particulates and dust matters by the neutral or positively charged surfaces may also be employed. There also methods which employ the activated carbon, molecular sieves, zeolites as the filtering material, or with the further application of ozone, oxidants, UV light, complementary with the photo-catalyst or other different catalyst materials to oxidize and decompose the pollutants by catalytic oxidation decomposition. Different purification methods have their respective own characteristics and performances. They may be used to deal with different kinds of pollutants. Nonetheless, the conventional market available air purifiers often employ more than one type of the purification methods and technologies. Regardless on which purification methods being employed, the filters being used in these air purifiers are usually arranged one by one in a parallel manner. A fan is usually equipped inside the air purifiers, for drawing or blowing the air from the upstream to the downstream positions, and forcing the air to pass through all the filter layers.

Different filters have different physical and chemical properties. The methods of purification such as filtration, adsorption or electrostatic precipitation are characterized with different filter static pressures, some filters have high static pressures, while some have low static pressures, some even do not possesses any static pressure at all. Owing to the fact that different sources of pollutants can be found at different levels, the air purification becomes a complicated subject.

The conventional arrangement of filter which the filters are arranged in a parallel manner, by the application of a single blower to draw or to blow the air across the filters, letting the pollutants to be treated by these layers of filters under one single air flow rate, can hardly enable the filters be functionalized completely and cost-effectively. In some case, the life-span of the downstream filters may become shortened due to the in-effective filtration of pollutants by the upstream filters. In some worse case, the downstream filters may become deteriorate or they would become the pools for incubating and further emitting the pollutants, which in reverse, further worsen the environmental pollution.

U.S. Pat. No. 6,248,146 proposes a different method of filter arrangement. Therein, the filters were not assembled in a parallel manner. In order to make the air flow through the secondary air filters (124), a primary throat aperture (106) is designed, when the air flow through the primary throat aperture (106), its speed will be accelerated. The pressure inside the secondary air guide (112) would be reduced, the outside air is then drawn through the secondary air filter (124) into the secondary air guide (112), wherein they are being mixed with the original airflow in the static regain section (116), through the output filter (126) the air is discharged. This patent does not explicitly described whether an exhaust fan or blower will be used. Nevertheless, whatever an exhaust fans or a blower being employed, the practical application of it still embedded with some significant disadvantages. If an exhaust fan is being used to draw the air out from the device, the primary throat aperture (106) will induce a high-frequency noise. If a blower is being used to blow the air into the device, apart from having the disadvantage of high-frequency noise being produced as mentioned, the device would need to have a even much more narrower primary throat aperture (106) compare to the case when the exhaust fan is being used, in order to ensure the secondary air guide (112) having sufficiently negative pressure effect for letting the outside air go through the secondary air filter (124). Further more, if a blower is being used, the motor torque for the blower should be of extraordinary large value, in order to overcome the drag effect caused by the resistance induced by the narrow primary throat aperture (106). The situation is similar to the case when the air is to blown through the a drinking straw with one's mouth, if one slightly flattened the middle of the straw with his fingers, then he would required to input much more energy to blow the air through the drinking straw. More energy will be consumed with higher motor torque, which apart from leading to higher cost of operation, the noise level of the devices will further be increased.

SUMMARY OF THE INVENTION

To solve the above problems, the present invention provides a method and an apparatus which enable the filters to be operated as per to their specific physical and chemical properties. Such properties include: filter static pressure, the filtration principles being concerns, the optimal air flow speed for effectively purification etc.

The main filter(s) being employed in the present invention is especially effective for certain purification where slow air flow rate is particularly required for achieving the best filtration effect. When being applied in the air purification where the adsorption method or the catalytic reaction is/are being adopted, the present invention gives the apparent results. The present invention also provides a method to extend the life span of the main filter in the air purification apparatus effectively.

In the present invention, it is the secondary air flow being entrained through the main filter instead of the primary air flow as being demonstrated in the traditional air purification methods. The secondary air flow rate can be varied by altering the speed of the blower(s) or the changing the speed of the related revolution device(s) in the apparatus. It can also be varied by altering any the following apparatus parameters: the size(s) of the air inlet(s), the size(s) of primary air flow inlet(s), the size(s) of the secondary air flow inlet(s), the orientation(s) of the main filter(s), the orientation(s) of the auxiliary filter(s), and the size of the air outlet(s) of the apparatus, etc. Therefore, the air purification apparatus can be designed with high flexibility. The main filter can always be allowed to operate under an effective air flow rate and achieving the best purification result. The performance of the main filter will not be affected nor will its life span be shortened when it is to be matched with other filters in the apparatus, or in the case where the air flow rate which generated by the blowing device is changed due to the further matching of other filters. More progressively, as the main filter and the blowing device are not being arranged in a parallel manner, the alteration the main filter characteristics such as its resistance towards the air flow and the alteration of the main filter properties such as its respective thickness, will not affect the original loading of the blowing device. Therefore, the present invention further offers an environmental friendly method for purification. To any existing environment device(s) that already been equipped with blower(s) or any rotating device(s), such as fan, exhaust fan, air cooling machine, air-conditioning machine, heater, the air outlet of the air-conditioner inside a vehicle, or any conventional air purifier etc., the further mounting of a main filter as described in the present invention to the air inlet or the air outlet of the environment device will make the environment device become an air purification apparatus, however, without increasing the motor loading of the existing blower or the rotating component. The mentioned main filter which being mounted onto the environment device, apart from having its shape to be matched with the environment device for the purpose of installation, the thickness and shape of the main filter, as well as the angle and orientation between the main filter and the said environment device during installation shall be match to allow the secondary air flow be adjusted intelligently, making the environment device a smart air purification apparatus.

The air purification method is being realized as present in this invention.

An air purification apparatus comprising:
a casing,
at least one apparatus air inlet,
at least one apparatus air outlet,
at least one main filter,
at least one primary air flow inlet,
at least one secondary air flow inlet,
at least one device or method for drawing the primary air flow to flow from the upstream to the downstream positions, The primary air flow inlet and secondary air flow inlet are being positioned as the apparatus air inlet(s).

When the said primary air flow is drawn from upstream to the downstream within the casing, it is first from the primary air flow inlet where the primary air flow is being drawn in; the primary air flow subsequently is adapted to pass by at least one edge of an exterior of the main filter, causing at least two exterior surfaces of the main filter being exerted with different atmospheric pressures; the secondary air flow comprising the air with pollutants; through the secondary air flow inlet, a secondary air flow entrained into and passes through the main filter, from the exterior surface that being exerted with higher atmospheric pressure (i.e., main filter air inlet surface) to the exterior surface that being exerted with lower atmospheric pressure (i.e., main filter air outlet surface); the contaminated air is thereby being purified.

The air purification apparatus further comprising at least an exhaust port for venting the pressure. The exhaust port is located anywhere appropriately on the casing. When the rotating speed of the fan or blower is too high, and high up to condition that the airflow volume and airflow rate the secondary air flow cannot be attained accordingly subjected to the corresponding primary air flow which generated by the rotating speed of the fan or blower, the exhaust port will be adjusted to suitable aperture, allowing the outside air to flow into the casing or inside air to escape out of the casing through the said exhaust port.

The air purification apparatus further comprising at least one auxiliary filter.

The device(s) for drawing the primary air flow(s) from the upstream position to the downstream position is a fan or a rotating device of any type.

The said method for drawing the primary air flow from the upstream position to downstream position meaning to connect the apparatus of the present invention to another environment device which already comprised with an exhaust fan or a blower. The method of connection is that to mount the apparatus air inlet or the apparatus air outlet of the present invention to the air inlet or air outlet of the environment device, and achieving the purpose of drawing the air flow from the upstream to the downstream as mentioned in the present invention.

When the said fan is an exhaust fan, it is being installed at the downstream position of the main filter, and drawing the air from the upstream to the downstream positions within the casing. When the said fan is a blower or ventilation fan. It is being installed at the upstream position of the main filter, and blow the air from the upstream to the downstream positions within the casing. The performance of the air purification will be more apparent when an exhaust fan is in used, instead of when a blower or ventilation fan is in used. Less energy will be consumed to achieve the same air purification effect in the case when an exhaust fan. When an exhaust fan is in used to draw the air, no additional energy will be required as if in the case when a blower is in used, to overcome the air flow resistance by the casing. In opposite, unwanted air flow resistant will be resulted by the rebounding of air flow volume within the casing, when a blower or a ventilation fan is in used and when the air flow volume is too high for the casing to accommodate or for the air flow to pass through. Motor with high torque value shall be used when a blower or ventilation fan is in used, to deliver the air to the apparatus air outlet. Apart from consuming more energy, noise will be produced; the turbulent flow may eventually lowered the secondary air flow rate. Nonetheless, no matter an exhaust fan, a blower or a ventilation fan is in used, it will still achieve the spirit as describes in the present invention.

The rotating device which draw the primary air flow from the upstream to the downstream positions may also be a device can be mounted directly onto the main filter. The main filter is brought to rotate together with the said device during the operation of the device. The primary air flows are then drawn from the upstream to the downstream positions, the primary air flows pass by at least one edge of an exterior surface of the main filter and causing at least two exterior surfaces of the main filter being exerted with different atmospheric pressures; a secondary air flow is entrained to pass through the main filter, from air in side to its air out side of the main filter; the contaminated air is thereby being purified.

The air purification apparatus of the present invention can further be regarded as a basic unit. A plurality of basic units may further combine and operate together. The combination method is in a way that the apparatus air outlet of one basic unit being connected wholly or partially to the apparatus air inlet(s) of other basic unit(s).

The primary air flow inlet, the secondary air flow inlet and the apparatus air inlet of the present air purification apparatus further comprising any one of the following features:
1. The primary air flow inlet and secondary air flow inlet are originated from the same apparatus air inlet; or
2. The primary air flow inlet and secondary air flow inlet are originated separately from the different apparatus air inlet; or
3. The two characteristics of above coexist.

Different primary air flows which adjacent to the air inlet and the air outlet of the main filter will be formed by one or more of the following methods, and resulting different atmospheric pressures at the two exterior surfaces of the main filter:
1. Using at least one fan or blower to create different primary air flows.
2. Creating the different primary air flows by employing a main filter bearing different inner and outer profile surfaces at its cross-section view.
3. Creating the different primary air flows by employing a main filter bearing different materials and/or having different roughness at its air inlet and air outlet surfaces.
4. By adjusting one or more of the following parameters to creates different primary air flows:
    to open or close, the aperture size and the orientation of the apparatus air inlet; the size and the orientation of the primary air flow inlet; the size and the orientation of the secondary air flow inlet; the dimensions on length, width, thickness, height etc., of the casing; the width, the length and the orientation of the passage within the casing that allow the primary air flow to flow through; the orientation of the main filter; the orientation of the auxiliary filter; the speed of the rotating device that drive the primary air flow to flow from the upstream to the downstream positions within the apparatus.
    When the secondary air flow inlet is being adjusted to closed position, the secondary air flow volume that being entrained into the main filter will also become zero. When the main filter is a filter for gaseous phase pollutants removal by catalytic oxidation and the auxiliary filter is a filter for particulate phase pollutants removal, the secondary air flow inlet may be adjusted to closed position when the concentrations of particulate phase pollutants are too high and will damage the life of the main filter. All the air will be forced to pass through the auxiliary filter for particulate phase pollutants removal in an advanced. Until the concentration of the particulates phase pollutants reaches to a satisfactory level, then the secondary air flow inlet will be opened for the removal of gaseous phase pollutants by the main filter and the further removal of the remaining particulate phase pollutants by the auxiliary filter. With the adjustment on secondary air flow inlet, the present invention allows the air purification to be performed intelligently, systematically and effectively based on the concentration of the pollutants in the environment.
    By adjusting (i) the dimension on length, width, thickness and height etc. of the casing, and/or (ii) by modifying the width, the length and the orientation of the passage within the casing that allow the primary air flow, will alters the primary air flow volume and primary air flow rate. The air flow volume and rate of the secondary air flow, as well as the orientation and the direction of the secondary air flow will be changed by (a) modifying the direction and orientation of the primary filter and/or (b) changing the primary air flow volume and air flow rate.
    In addition, fine-tuning the orientations of the main filter and the auxiliary filter within the apparatus will vary the air flow path for the primary air flow and/or the secondary air flow, which further adjust of the atmospheric pressures that being exerted on the main filter during the time when the primary air flow passes by it, which will further regulate rates and volume of the secondary air flow.

The method of adjustment mentioned above meaning to adjust either manually or automatically by electronic control, or to adjust by both manually and automatically.

The air purification apparatus may further comprising a central processing unit.

The air purification apparatus may further comprising one or a plurality of environment sensors. The sensor(s) may be used to measure any one of the temperature, humidity, volatile organic compounds, formaldehyde, carbon dioxide, carbon monoxide, dust particle, ozone, nitrogen oxides, airborne bacteria, radon, air flow rate, air flow volume, atmospheric pressure, luminance, noise level, and radiation.

The method to adjust automatically by electronic control meaning to adjust and determine base on the data obtained by the environmental sensors, or base on the pre-implemented computer program in the central processing unit, and then operate the apparatus automatically. The computer program further comprising one or a plurality modes of operation, e.g. a dust removal mode for particulate phase pollutants removal or various size of particulate contaminants removal by auxiliary filter; a volatile organic compounds contaminants removal mode, odor removal mode or various types of gaseous phase pollutants removal mode for gaseous phase pollutants removal by main filter. A sterilization mode may further be included which allow the apparatus to be operated in coordination with a UV lamp. A sleeping mode may also be included which purposely reduce the volume of the air flow in order to reduce the noise level.

In the present invention, the main filter(s) and the auxiliary filter(s) being installed in the air purification apparatus further possess one or more the difference:
    different filtering principle,
    different optimal filtration air flow rate,
    different retention time towards pollutants by the corresponding filter,
    different air flow resistance,
    different filter density Regardless of the differences, the main filter and the auxiliary filter are always operated at their own respective ideal air flow rates to remove different types of pollutants under one primary air flow rate in the air purification apparatus.

Furthermore, using a main filter which bear higher density and higher air flow resistant in place of the original one will not give additional loading to the fan, nor increase the noise level of the apparatus. The contaminated air can still be effectively purified. The energy consumption is being low as before too.

In some embodiments, the main filter is a filter for treating the gaseous phase pollutants, odor or the organic contaminants.

In some embodiments, the auxiliary filter is a filter for filtering the particle phase pollutants.

In some embodiments, the auxiliary filter is a filter for removing the bacteria.

In some embodiment, the main filter possesses one of the following filtering materials:
1. materials contains activated carbon, photocatalytic, molecular sieve or the zeolite or the mixture contains thereof in any proportion; the materials may be in granular form and be put in a container of any shape which is penetrable by air.
2. materials being adhered with activated carbon, photocatalytic, molecular sieve or the zeolite or the mixture contains thereof in any proportion; the materials is penetrable by air
3. materials contains activated carbon, photocatalytic, molecular sieve or the zeolite or the mixture contains thereof in any proportion; the materials is in form of honeycomb structure.

In some embodiments, the air inlet or air outlet surfaces of the main filter further comprising at least a layer of other filter, which possesses different function in comparing to the main filter, such as a pre-filter to give further protect to the main filter, preventing the filtered pollutants from being blown out from the main filter.

The main filter in the present invention may also refers to a set of filters having different purification function and effectiveness. The set of filters are assembled in parallel manner.

In some embodiments, the air inlet or air outlet surfaces of the auxiliary filter further comprising at least a layer of other filter, which possesses different function in comparing to the auxiliary filter, such as a pre-filter.

The auxiliary filter in the present invention may also refers to a set of filters having different purification function and effectiveness. The set of filters are assembled in parallel manner.

In some embodiments, the auxiliary filter may be a device which employs the high-voltage to charge up the particulates and further collect them through the collector of the electrostatic precipitator.

The orientations of the main filter and auxiliary filter, shall conform to the main air flow in all possible way to avoid creating turbulence flow which may reduce the purification effect of the main filter.

The main filter may be a filter having an uniform thickness. The air inlet and air outlet profile surface from the vertical cross-section view is in parallel. The main filter may be a filter having a non-uniform thickness, the air inlet and air outlet profile surfaces by the vertical cross-section view being not in parallel manner.

In some embodiments, the main filter is a three-dimensional solid filter comprising one or a plurality of surface areas; the said three dimensional solid filter may be in circular shape of round ball or ellipse form, it may also be a three-dimensional solid filter which comprising any two or more of surface mentioned below:
  any planar surface;
  any regular or irregular two dimensional curving surface;
  any regular or irregular three-dimensional surface.
The three-dimensional solid filter further comprising one or a plurality of air inlet surface; one or a plurality of air outlet surface.

In some embodiment where the main filter is three-dimensional solid filter, if its air inlet surface is a two dimensional curving surface then its air outlet surface will be a two dimensional curving surface or a three dimensional curving surface; if its air inlet surface is a planer surface, then its air outlet surface may be a multi-planar surface, a two dimensional or three dimensional curving surface. In any case, the total surface area of the air inlet is smaller than that of the air outlet.

In some embodiments where the main filter is in the hollow cylindrical shape, the direction of the hollow void is preferable parallel to the direction of the primary air flow. The inner surface area and the outer surface area of the hollow cylindrical shaped main filter being the air inlet and the air outlet, or being the air outlet and the air inlet of the main filter respectively.

When the main filter is in the shape of hollow cylinder, the primary air which being drawn from the upstream to the downstream positions inside the casing will further adapted to pass by at least one of the below mentioned path(s):
1. The primary air flow only passes by the inner surface area of the hollow cylindrical main filter;
2. The primary air flow only passes by the outer surface of the hollow cylindrical main filter.
3. The primary air flows pass by both the inner and outer surfaces of the hollow cylindrical main filter.

In some embodiments where the main filter is in the shape of hollow cylinder, if the profile line at inner surface from its vertical cross-section view is longer than that at the outer surface, then the outer surface of the hollow cylindrical main filter will be the air inlet, and the inner surface will be the air outlet.

However, if the profile line at inner surface from its vertical cross-section view is shorter than that at the outer surface, then the inner surface of it will be the air inlet, and the outer surface will be the air outlet surface.

In some embodiments where the primary air flows are drawn to pass by both the inner and the outer profile surfaces of the hollow cylindrical main filter, and if the primary air flow rate adjacent to the inner profile surface is faster than the air flow rate adjacent to the outer profile line, then the outer surface of the cylindrical shaped main filter will be the air inlet, and the inner surface of the main filter will be the air inlet. In reverse, if the air flow rate adjacent to the inner profile surface of the hollow cylindrical main filter is slower than that at the outer profile surface, then the air inlet and air outlet of the main filter will be located at the inner surface and outer surface of the hollow cylindrical shaped main filter respectively.

In some embodiments of the said air purification apparatus where the auxiliary filter is being applied together with the main filter, no matter it is being assembled at the upstream or the downstream positions of the main filter, or be co-assembled at both the upstream and the downstream positions of the main filter, the orientation of the auxiliary filter(s) is being assembled to such a way that the primary air flow will pass through it directly. In the case where the auxiliary filter is located at the upstream position of the main filter, along with primary air flow, the air which contains the pollutants will first be drawn by the fan to pass through the auxiliary filter, the contaminated air is being initially purified by the auxiliary filter. This initial purified air will then, subsequently at the downstream position, be merged and multiplied with the purified air which is being discharged from the main filter. In the case where the auxiliary filter is located at the downstream position of the main filter, the purified air which is discharged from the main filter will be merged with the primary air flow, and subsequently at the downstream position be further purified by the auxiliary filter. Double purification on polluted air is therefore be performed in this case.

In some embodiments of the said air purification apparatus, the auxiliary filter is being applied together with the main filter, no matter it is being assembled at the upstream or the downstream positions of the main filter, or be co-assembled at both the upstream and the downstream positions of the main filter, the auxiliary filter(s) and the main filter are arranged in series manner. When the primary air is drawn from the upstream to the downstream positions by the fan, it will flow and passes by at least one edge of the auxiliary filter, two exterior surfaces of the auxiliary filter are exerted with different atmospheric pressures. The air with pollutants are entrained to pass thought the auxiliary filter by the secondary air flow, from the side of the auxiliary filter with higher atmospheric pressure to the side which have lower atmospheric pressure. The contaminated air is thereby being purified. The air purified by the auxiliary filter further be merged and be combined with the air which purified by the main filter.

In the air purification apparatus, the auxiliary filter may be further assembled in one or more of the following position(s):
1. It is being placed in front of the air inlet side of the main filter, and be arranged with the main filter in a parallel manner.
2. It is being placed after the air outlet side of the main filter, and be arranged with the main filter in a parallel manner.

In the case where the auxiliary filter is being assembled in front of the air inlet surface of the main filter, and when the fan is being operated, the primary air flow is drawn to flow from the upstream to the downstream positions within the casing, the primary air flow is adapted to passe by one edge the exterior of the main filter, and making the atmospheric pressure at the surface of this exterior be difference in comparing to that in one surface of the auxiliary filter, the secondary air flow with the contaminants will entrain through to the auxiliary filter from the surface bearing the higher atmospheric pressure, and subsequently to the air inlet surface of the main filter, which then further pass through the main filter to the surface of it which bearing lower atmospheric pressure. The contaminated air is therefore being purified.

In the case where the auxiliary filter is being assembled at the back of the air outlet surface of the main filter, and when the fan is being operated, the primary air flow is drawn to flow from the upstream to then downstream positions within the casing, the primary air flow is adapted to by one edge of the exterior of the auxiliary filter, and making the atmospheric pressure at the surface of this exterior be difference in comparing to that in one surface of the main filter, the air with contaminants will enter to the main filter from its higher pressure side to the air inlet surface of the auxiliary filter, which then further flow to the surface of the auxiliary filter that bearing the lower atmospheric pressure. The contaminated air is therefore being purified.

The said air purification apparatus may further comprising two auxiliary filters, one auxiliary filter and the main filter are arranged in a parallel manner, while another auxiliary filter and the main filter are arranged in a series manner. When the fan is being operated, the primary is will be drawn to flowed from the upstream to the downstream positions within the casing, the secondary air flows are form and entrained to pass through the follow individually:
(a) the main filter; and
(b) the auxiliary filter, which being arranged in series with the main filter.

Both secondary air flows is further merged and multiplied with the primary air flow at the downstream position before being discharged. The contaminated air is therefore being purified.

The said air purification apparatus comprising at least two auxiliary filters. At least one auxiliary filter being arranged in such a way it will be passed through by the primary air flow, when the primary air flow is generated and is drawn from the upstream to the downstream positions by the operation of the fan. Another auxiliary filter being arranged in such a way that it is in parallel with the primary filter, either being placed in front of the air inlet surface or after the air outlet surface of the main filter. The air with pollutants are being purified separately by the following two different paths:
1. The air with pollutants is drawn to pass through axillary filter by the air flow which generated from the operation of the fan, by directly passing through at least one of the said auxiliary filter, the air is being purified.
2. The air with pollutants is being purified by the auxiliary filter and the main filter, which the two filters are assembled and arranged in parallel manner.

The purified air from the two paths are being merged and multiplied at the downstream position, subsequently be discharged to the environment.

The said air purification apparatus further comprising at least two auxiliary filters, at least one auxiliary filter being arranged in such a way that it is passed through by the primary air flow, which is generated and is drawn to flow from the upstream to the downstream positions by the operation of the fan. Another auxiliary filter being arranged in such a way that it is in series with the primary filter, either being placed the upstream or the downstream positions of the main filter. The air with pollutants are being purified separately by the following three different paths:
1. The air with pollutants, along with the main air flow which generated by the operation of the fan, being first drawn to pass through auxiliary filter, and being initially purified.
2. The air with pollutants, entrained along with the secondary air flow, passed through the auxiliary filter, from the exterior with higher atmospheric pressure to the exterior with lower atmospheric pressure.
3. The air with pollutants, entrained along with the secondary air flow, passed through the main filter, from the exterior with higher atmospheric pressure to the exterior with lower atmospheric pressure.

The purified air from the two paths are being merged and multiplied at the downstream position, subsequently be discharged to the environment.

The said air purification apparatus further comprising at least three auxiliary filters, at least one auxiliary filter being arranged in such a way that it is passed through by the primary air flow, which is generated and is drawn to flow from the upstream to the downstream positions by the operation of the fan; at least one auxiliary filter being arranged in such a way that it is in parallel with the primary filter, either being placed in front of the air inlet surface or after the air outlet surface of the main filter; at least one auxiliary filter being arranged in such a way that it is in series with the primary filter, either being placed the upstream or the downstream positions of the main filter. The air with pollutants are being purified separately by the following three different paths:

1. The air with pollutants, along with the main air flow which generated by the operation of the fan, being first drawn to pass through auxiliary filter, and being initially purified.
2. The air with pollutants, along with the secondary air flow, being entrained pass through the auxiliary filter, from the exterior with higher atmospheric pressure to the exterior with lower atmospheric pressure.
3. The air with pollutants is being purified by the auxiliary filter and the main filter, which the two filters are assembled and arranged in parallel manner.

The purified air from the three paths are being merged and multiplied at the downstream position, subsequently be discharged to the environment.

Different auxiliary filters may further co-ordinate and be assembled together and form one foremost auxiliary filter. The foremost auxiliary filter have one or more than one of the following characteristics:

Partial or whole of the foremost auxiliary filter being arranged in parallel with the main filter;
Partial or whole of the foremost auxiliary filter being arranged in series with the main filter;
Partial or whole of the foremost auxiliary filter being arranged in such a way that that being passed through by the primary air flow, which is generated and is drawn to flow from the upstream to the downstream position by the operation of the fan.

The air purification apparatus may further comprising at least one of the following air purification component, in any position of the apparatus for further purifying the air:

High voltage electrostatic precipitator;
Negative ion generator;
Positive ion generator;
Ozone generator;
Oxidant generator;
Filter comprising the activated carbon, photocatalyst, zeolite or molecular sieves, or the mixtures of the any materials thereof in any form or filter type;
Device with water scrubbing;
Ultra Violet light device.

The air purification apparatus may further comprising at least one air purification component from the negative ion generator, ozone generator, oxidant generator; the air purification component be assembled at the upstream position of the main filter, and the main filter is a filter which need the oxidants or reactive oxygen species to carry out the catalytic oxidation reaction within itself.

The air purification apparatus may further comprising at least one Ultra Violet lamp being assembled at the upstream position of the main filter, the gases phase pollutants and oxidants or the reactive oxygen species first be activated before entering to the main filter. The catalytic oxidation reaction within main filter is then performed in a more effective way.

The air purification apparatus further operates in co-ordinate with different environment device, such as heater, cooler, air conditioner, humidifier, dehumidifier, kitchen exhaust hood, hand dryer, food decomposer, compost machine, pet houses and shoes cabinet etc.

The said an air purification apparatus, when being used as a device for removing the radiation substance from the air, the casing shall be materials or being coated with materials that do not leak the radiation substances.

The said an air purification apparatus, when being used as a device for remove the radiation substance from the air, the air outlet surface of the main filter shall contain an anti-radiation layer to prevent the leak of radiation substance.

Since total volume of air flow out should be equal to the total volume of the air flow in to the air purification apparatus, by adjusting the air inlet and air outlet of the apparatus, the primary air flow inlet and/or the secondary air outlet will effective control of the air flow rate and volume of the secondary air flow.

The relationship of these parameters are calculate with the following equation:

$$V_{wm1} = V_{main1} \times n_{A1} \times k_{v1} \times C_3 \qquad \text{Equation 1:}$$

$$V_{wm2} = V_{main2} \times n_{A2} \times k_{v2} \times C_4 \qquad \text{Equation 2:}$$

When exhaust fan is being used:

$$\text{Volume Out} = \text{Volume In} + \text{leakage In} \qquad \text{Equation 3:}$$

$$V_{wm1} \times A_{m1} + V_{wm2} \times A_{m2} = \text{Volume In} + \text{Leakage In} \qquad \text{Equation 4:}$$

When blower or ventilation fan is being used:

$$\text{Volume Out} + \text{leakage Out} = \text{Volume In} \qquad \text{Equation 5:}$$

$$V_{wm1} \times A_{m1} + V_{wm2} \times A_{m2} + \text{leakage Out} = \text{Volume In} \qquad \text{Equation 6:}$$

The parameters of the above equations 1-6 are defined as follows:

Volume Out: Total Air Out Volume
Volume In: Total Air In volume
Leakage In: The total air volume of the air, without going through the air inlet of the apparatus, and leak into the apparatus
Leakage Out: The total air volume of the air, without going through the air outlet of the apparatus, and leak out from the apparatus
$V_{wm1}$: primary air flow rate (which passes by the air outlet surface of the main filter)
$V_{wm2}$: primary air flow rate (which passes by the air inlet surface the main filter)
$V_{main1}$=primary air flow rate at the profile line adjacent to the air outlet surface of the vertical cross section of the main filter
$V_{main2}$=primary air flow rate at the profile line adjacent to the air inlet surface of the vertical cross section of the main filter
$A_{m1}$: Cross section area of the primary air flow inlet
$A_{m2}$: Cross section area of the secondary air flow inlet
$n_{A1}$ is the normal unit vector pointing into the air outlet of the main filter
$k_{v1}$ is the vertical unit vector, normal to the primary air flow direction of $V_{wm1}$
$n_{A2}$ is the normal unit vector pointing into the air inlet of the main filter
$k_{v2}$ is the vertical unit vector, normal to the primary air flow direction of $V_{wm2}$
$C_3$=Constant 3 in the apparatus
$C_4$=Constant 4 in the apparatus The following equation of calculation showing the relationship between the primary air flow rate and the pressure different between the two exterior surfaces:

$$P_{in} [\tfrac{1}{2} \times \rho \times V_{main1}^2] = P_{out} + [\tfrac{1}{2} \times \rho \times V_{main2}^2] \qquad \text{Equation 7}$$

The definition of the parameters stated in the equation are as follows:

$P_{in}$=The atmospheric pressure at the air inlet surface of the primary filter
$P_{out}$=The pressure at the air outlet surface of the primary filter
$V_{main1}$ The primary air flow rate at the profile line adjacent to the air inlet surface of the primary filter $V_{main2}$=The primary air flow rate at the profile line adjacent to the air outlet surface of the primary filter ρ=density of the air Base on the following equation, the relationship of the thickness, the cross-section area, the air flow rate of the secondary air flow is defined:

$$(P_{in}-P_{out}) \times D = (1/2) \times v^3 \times \rho * C_1 + C_2 \qquad \text{Equation 8}$$

The parameters stated in the above equation 8 are being defined as below:

$P_{out}$=the atmospheric pressure at the air outlet surface of the main filter $P_{in}$=the atmospheric pressure at the air inlet surface of the main filter D=the thickness of the main filter where being traveled by the secondary air flow $C_1$=Constant 1 of the apparatus $C_2$=Constant 2 of the apparatus β=Density of air v=The air flow rate of the secondary air flow, when it is passing through the main filter The said air purification apparatus may further be applied in an apparatus for water purification system or fluid system, the said apparatus further defines: the air flow inlet as the fluid inlet of the apparatus;

the air flow outlet as the fluid outlet of the apparatus;

the fan as the device is used to draw the fluid flow from the upstream to the downstream positions of the apparatus;

wherein said apparatus of water or fluid purification system further comprising at least one primary flow inlet and at least one secondary flow inlet.

When the apparatus is in operation, the primary fluid flow will be drawn to flow from the upstream to the downstream positions; the primary fluid flow will be drawn to flow into the apparatus through the fluid inlet, it then adapted to pass by one edge of the exterior surface of the main filter, the main filter subsequently having two sides of it be exerted with different fluid pressure; a secondary fluid flow which contains the pollutants, first through the secondary fluid inlet, go into and passes through the main filter, from the surface which is being exerted with higher fluid pressure to the surface which is being exerted with lower fluid pressure (the air outlet of the main filter), the contaminated fluid is therefore being purified.

The present invention further comprising a method of air purification, the said method shall include the employment of any of the above mentioned system of apparatus, and achieving the purpose of air or fluid purification.

BRIEF DESCRIPTION OF THE DRAWINGS

FIGS. 15-54 present the structural schematic diagrams for the embodiments 7 to 46 of the present invention;

DETAILED DESCRIPTION OF THE EMBODIMENTS

Figure 1:
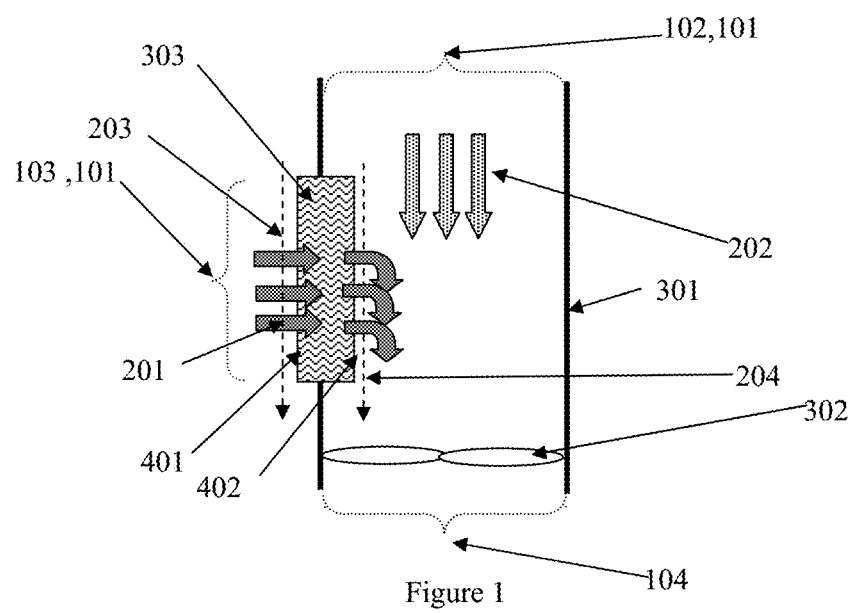
FIGS. 1-6 present the structural schematic diagrams for the embodiments 1 to 6 of the present invention.

FIG. 1 illustrates one embodiment of an air apparatus. The air purification apparatus comprising: a casing 301, a plurality of apparatus air inlets 101; an apparatus air outlet 104, a main filter 303, a fan 302, a primary air flow inlet 102 and a secondary air flow inlet 103. The primary air flow inlet 102 and the secondary air flow gas flow inlet 103 in the present embodiment are being positioned as the apparatus air inlets 101. As shown in this embodiment, the primary air flow inlet 102 and the secondary air flow inlet 103 are originated from different air inlets 101 of the apparatus. The air purification apparatus further comprising a pressure exhaust port 106. When the rotating speed of the fan or blower is too high for the corresponding airflow volume and airflow rate of the primary and secondary air flow to be attained in according to the rotating speed of the fan or blower, the pressure exhaust port 106 will be adjusted to suitable aperture and allows the outside air to flow in or inside air to escape out of from the casing through the said exhaust port 106. The profile lines at the air inlet surface 401 of and the air outlet surface 402 from the vertical cross-section view of the main filter 303 in the present embodiment are being in a parallel manner. When the fan 302 is being operated, it drives the primary air flow 202 to flow from the upstream to the downstream positions within the casing 301. The primary air flow 202 being drawn into the apparatus through the primary air flow inlet 102. The primary air flow 202 subsequently is adapted to pass by at least one edge of the exterior of the main filter 303. When the primary air flow 202 passes by the inner line of the profile surface as shown from the vertical cross-section view of the primary filter 303, the air flow 204 rate adjacent to the inner profile surface is higher than the air flow 203 rate adjacent to the outer profile surface. Subsequently, at least two surfaces, 401 and 402, of said primary filter are being exerted at different atmospheric pressures. A secondary air flow 201 comprising the air with pollutants is formed. Through the secondary air flow inlet 103, the secondary air flow 201 being entrained to enter the main filter 303, flow from the side of higher atmospheric pressure (the air inlet 401 of the main filter) to the side of lower atmospheric pressure (the air outlet 402 of the main filter), the contaminated air is therefore being purified.

Figure 2:
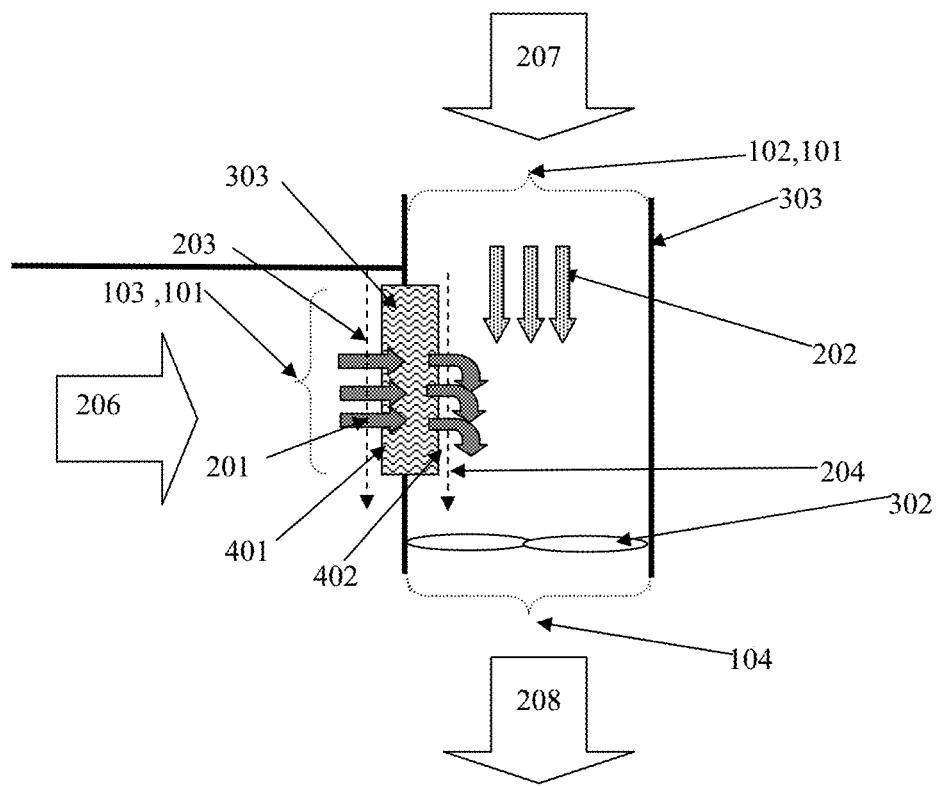

FIG. 2 illustrates another embodiment of the air purification apparatus. The basic structure of this embodiment is same to that as described in the FIG. 1. In this example, the air purification apparatus being regarded as a fresh air supply, wherein a wall 306 is being used to separate the plurality of apparatus air inlets. The wall 306 may be a part of the casing 301, or other barrier materials which is being added intentionally during the installation of the air purification apparatus of the present invention. Outdoor fresh air often bears higher temperature and higher humidity compared to indoor conditioned air. To save the energy, when drawing in the untreated fresh air 207 from the outdoor, a certain portion of the indoor conditioned and dried air 206 will be further purified by the main filter 303 along with the secondary air flow 201; along the secondary air flow 201, the purified air being discharged by main filter will further be merged and multiplied with the primary air flow 202, forming a multiplied air 208. The multiplied air 208 may further be recirculated and return to the indoor environment.

Figure 3:
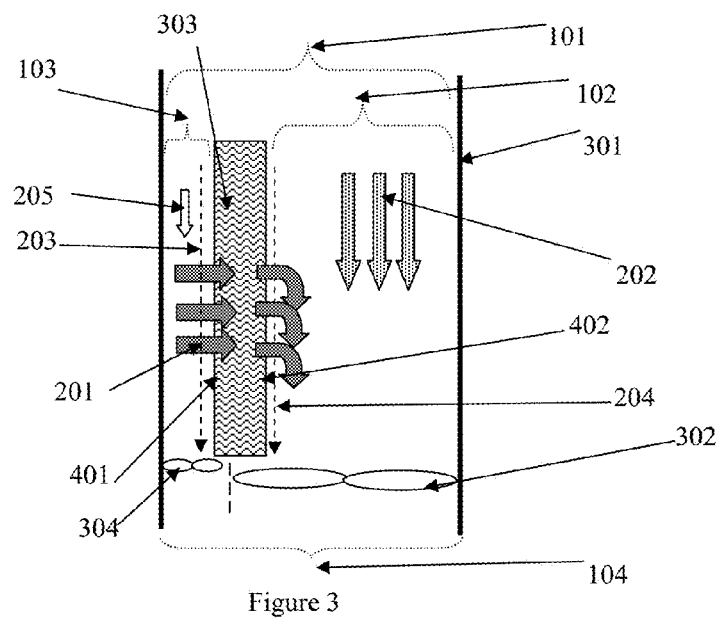

FIG. 3 illustrates another embodiment of the air purification apparatus. The air purification apparatus comprising: a casing 301, an apparatus air inlet 101; an apparatus air outlet 104, a main filter 303, a fan 302, a primary air flow inlet 102 and a secondary air flow inlet 103. The primary air flow inlet 102 and the secondary air flow gas flow inlet 103 in the present embodiment are originated from one air inlet 101 of the apparatus. When the fan 302 is being operated, it drives the primary air flow 202 to flow from the upstream to the downstream positions within the casing 301. The primary air flow 202 being drawn into the apparatus through the primary air flow inlet 102. The primary air flow 202 subsequently adapted to pass by at least one edge of the exterior 402 of the main filter 303. When the primary air flow 202 and 205 pass by at least one edge of the air inlet surface 401 and at least one edge of the air outlet surface 402 of the main filter 303, the air flow 204 rate adjacent to the inner profile surface is faster than the air flow 203 rate adjacent to the outer profile surface. Subsequently, at least two surfaces 401 and 402 of the primary filter 303 are being exerted at different atmospheric pressures. A secondary air flow 201 comprising the air with pollutants is formed. Through the secondary air flow inlet 103, the secondary air flow 201 is being entrained to enters the main filter 303, from the side of higher atmospheric pressure (the air inlet surface 401 of the main filter) to the side of lower atmospheric pressure (the air outlet surface 402 of the main filter), the contaminated air is therefore being purified.

Figure 4:
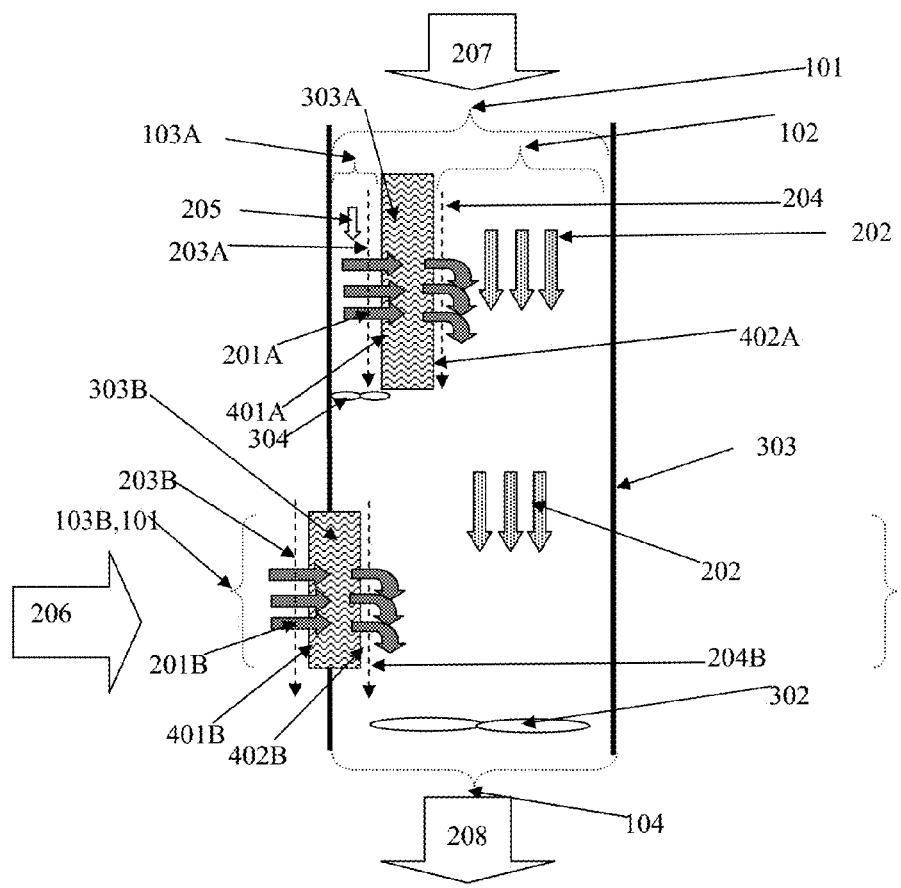

FIG. 4 illustrates another embodiment of the air purification apparatus. The air purification apparatus comprising: a casing 301, a plurality of apparatus air inlets 101; an apparatus air outlet 104, two main filters 303A and 303B, two fans 302 and 304, a primary air flow inlet 102 and a plurality of secondary air flow inlets 103A and 103B. When the fan 302 & 305 are being operated, it drives the primary air flows 202 and 205 to flow from the upstream to the downstream positions within the casing 301. The primary air flows 202 and 205 being drawn into the apparatus through the primary air flow inlets 102 and the secondary air flow inlet 103A. The primary air flows subsequently pass by two edges of the exteriors 401A and 402A of the main filter 303B and one edge of the exterior 402 of the main filter 303B.

The rates of the air flows 204A and 204B adjacent to the inner profile surface of the main filter 303A and 303B are faster than the rates of the air flows 203A and 203B, which adjacent to the outer profile surfaces of the main filter 303A and 303B. Subsequently, at least two surfaces (401A and 402A, 401B and 402B) of the primary filters are being exerted at different atmospheric pressures. Two secondary air flows 201A, 201B are formed. Through the secondary air flow inlets 103A and 103B, the secondary air flows 201A and 201B enter the main filters 303A and 303B from the sides of higher atmospheric pressures to the sides of lower atmospheric pressures, the contaminated air is therefore being purified.

As shown in the above four embodiments, the primary air flow inlet 102, the secondary air flow inlets 103A & 103B, and the apparatus air inlets 101, having the following two characteristics be co-existed: (1) The primary air flow inlet 102 and the secondary air flow inlet 103A originated from the same apparatus air inlet 101; (2) the primary air flow inlet 102 and the secondary air flow inlet 103 originated from different apparatus air inlets 101.

The fourth embodiment mentioned above comprising two basic structures, the upper structure is basically same as that being mentioned for the third embodiment, while the lower structure is basically same as that being mentioned for the first embodiment. The air purification apparatus mentioned in this invention may further be regarded as one basic unit. When more than one basic units are being assembled together, some component(s) in the basic unit(s), for example the fan(s) or device(s) for drawing the air to flow from the upstream to the downstream positions may further be omitted. The assembling can be in the way that partial or whole of the apparatus air outlet(s) be connected to partial or whole of the apparatus air inlet(s) of another unit.

Figure 5:
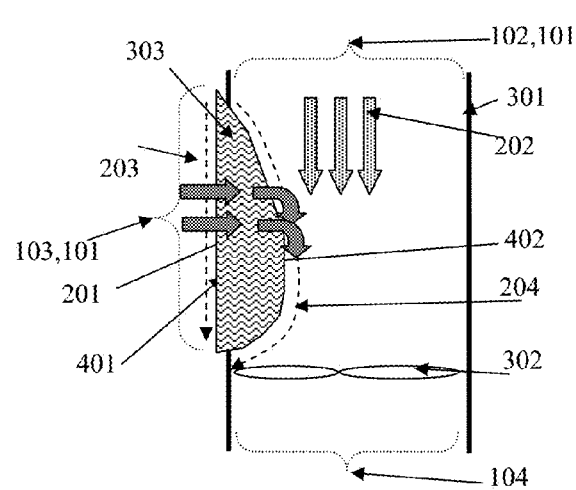
Figure 6:
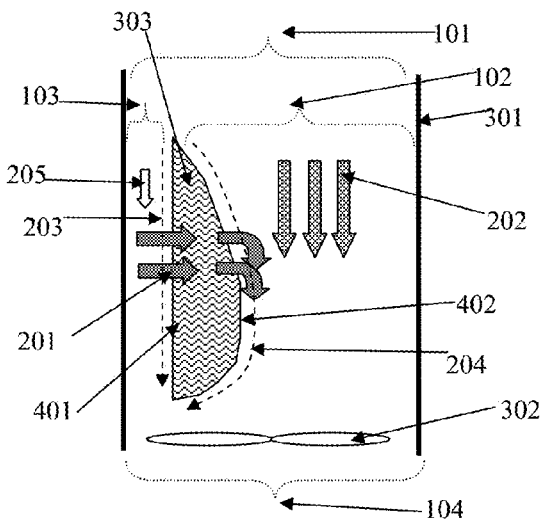

FIG. 5 and FIG. 6 illustrates two other embodiments of the air purification apparatus. In the embodiment being shown in the FIG. 5, the primary air flow inlet 102 and the secondary air flow inlet 103 are originated from different apparatus air inlets 101. In the embodiment being shown in the FIG. 6, the primary air flow inlet 102 and the secondary air flow inlet 103 are originated from the same apparatus air inlet 101. Both embodiments shown in the FIGS. 5 and 6 applied the same three dimensional solid main filter as indicated in the FIG. 7. The lines at the profile surface of the air inlet surface 401 and that at the air outlet surface 402 are not being in a parallel manner. When the primary air flows 202 and 205 pass by the air outlet surface 402 of the primary filter 303, the rate of the air flow 203 which adjacent to the air inlet surface 401 is slower in comparing to the rate of the air flow 202 which is adjacent to the air outlet surface 402. Different atmospheric pressures are therefore obviously being induced at both the air inlet surfaces and air outlet surface of the main filter 303. A secondary air flow 201 comprising the air with pollutants is formed. Through the secondary air flow inlet 103, the secondary air flow 201 is being entrained to enter the main filters 303 from the side with higher atmospheric pressure (the air inlet surface 401 of the main filter) to the side with lower atmospheric pressure (the air outlet surface 402 of the main filter), the contaminated air is therefore being purified.

Figure 7:
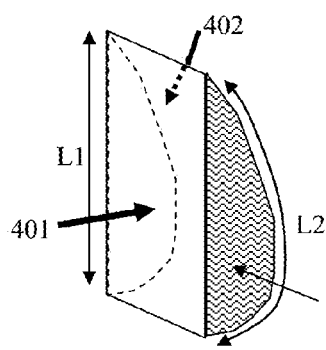
FIGS. 7-14 present the schematic diagram of different shapes of the main filter being employed in the air purification apparatus of the present invention.
Figure 8:
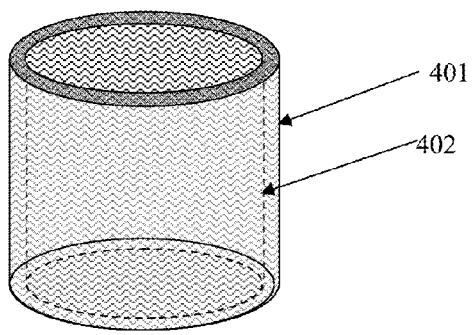
Figure 9:
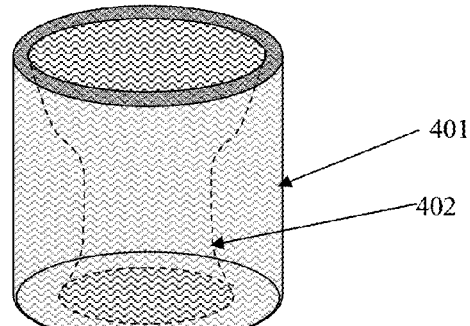

Apart from employing the three dimensional solid filter 303 indicated in FIG. 7, the main filter may further be in the form of a hollow cylindrical filter (as indicated in FIG. 8 and FIG. 9). FIG. 8 indicated a hollow cylindrical filter having the even thickness. The profile line of the air inlet surface 401 is parallel to the profile line of the air outlet surface 402. FIG. 9 also indicated a hollow cylindrical filter which bearing an uneven thickness. The profile surface of the air inlet surface 401 is not parallel to the profile surface of the air outlet surface 402. In the FIG. 9, the profile surface at the inner surface is longer than the profile surface at the outer surface. When the main filter as shown in FIG. 9 is being assembled into the $8^{th}$ and $9^{th}$ embodiments (as shown in FIGS. 8 and 10), the outer surface of the hollow cylindrical filter will become the air inlet surface 401, and the inner surface of it will become the air outlet surface 402.

Figure 10A:
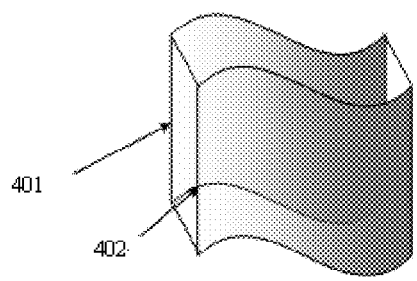
Figure 10B:
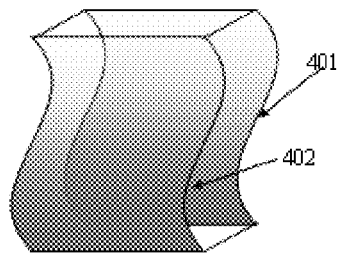

FIG. 10 indicates two other filters which bearing the two-dimensional curving surfaces at both of their sides. The two filters bear the uniform thickness. The non-planer profile increase the surface area for air inlet and air outlet. The main filter 303 may either installed vertically or horizontally onto the air purification apparatus of the present application. When the main filter 303 is being applied in a vertical orientation (as shown in FIG. 10B), the inner profile line and outer profile lines from its vertical cross-section view are not straight lines, however, being in parallel with each other. When the main filter 303 is being applied in a horizontal orientation (as shown in FIG. 10A), the inner profile line and outer profile lines from the vertical cross-section view of this solid three-dimensional main filter 303 are straight lines and being in parallel with each other. Assembling the main filter 303 in a horizontal orientation allow the primary air flow to travel smoothly, avoiding turbulence flows to be arouse adjacent to the profiles lines of both air inlet surface 401 and air outlet surface 402.

Figure 11:
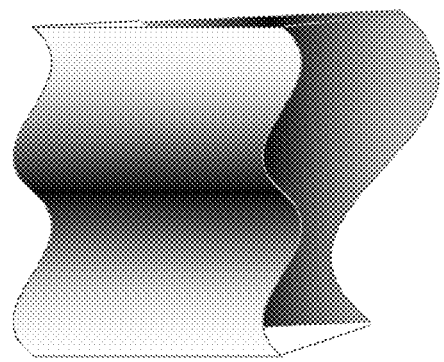
Figure 12:
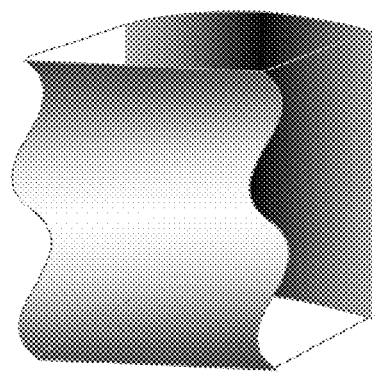

FIG. 11 and FIG. 12 indicates two main filters which comprise two two-dimensional surfaces 402 and 401 for the secondary air flow inlet and the air secondary air outlet. When this solid filters being assembled in a vertical orientation, a profile surface of the air outlet from its vertical cross section view, being a straight lines as indicated in FIG. 11; both profile surface from the vertical cross-section view, as indicated in FIG. 12 are curving surface. When the primary air flow passes by the air outlet surface of the main filter 303 as shown in FIG. 11, it is travelling smoothly and created less turbulence flow.

Figure 13:
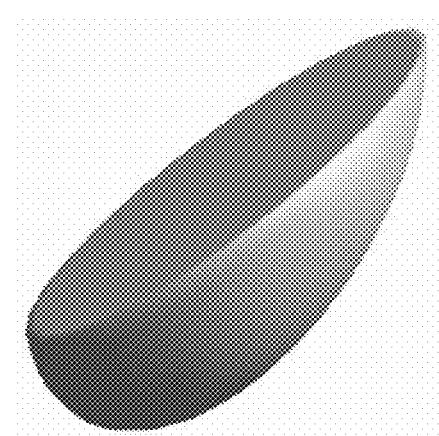

FIG. 13 indicates a three-dimensional filter which comprising a planar and a three-dimensional surfaces. The three dimensional surface is where the air outlet located and the planer surface is where the air inlet located. When the primary air flow passes by the surface profile of the air outlet, the air flow adjacent to the surface profile of the air inlet bearing a slower rate in comparing to that at the surface profile of the air outlet. Hence, the air outlet surface and air inlet surface of the main filter are being exerted with different atmospheric pressures.

Figure 14:
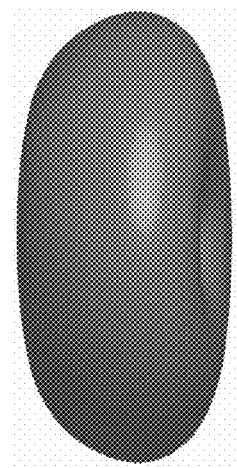

FIG. 14 indicates another solid three-dimensional filter. Only if when the primary air flow is adapted to pass by at least one edge of the exterior surface of the main filter, at least two surfaces of the main filter will be exerted with different atmospheric pressure, and the secondary air flow will then be formed and entrained to pass through the main filter, from surface that bearing with higher atmospheric pressure (air inlet side of the main filter) to the surface that bearing with lower atmospheric pressure (air outlet side of the main filter), the contaminated air is thereby being purified. And the objective of the present invention is therefore achieved.

Figure 15:
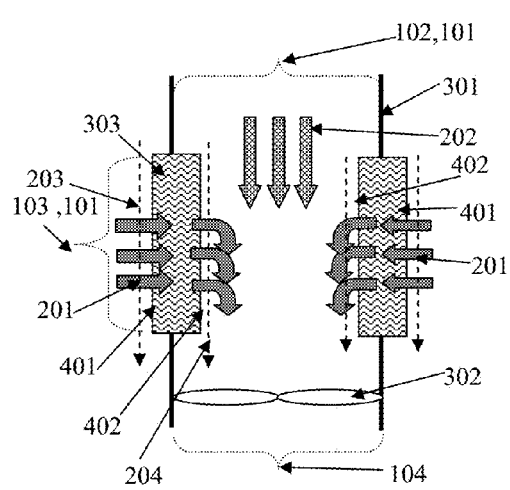
Figure 17:
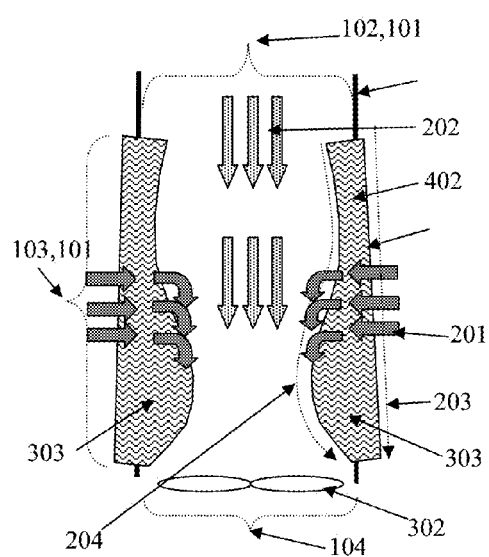

FIG. 15 and FIG. 17 indicated the embodiments of 7 and 8. The former employed the hollow cylindrical main filter which is shown in the FIG. 8, while the latter employed the hollow cylindrical main filter which is shown in the FIG. 9. The air purification apparatus comprising a casing 301, a plurality of air inlets 101 of the apparatus, and apparatus air outlet 104, main filter 3030, fan 302, the primary air flow inlet 102 and secondary air flow inlet 103. The primary air flow inlet 103 and secondary air flow inlet 103 is positioned as the air inlets 101 of the apparatus. As indicated in the figures, the primary air flow inlet 102 and the secondary air flow inlet 103 are originated from different air inlets 101 of the apparatus. When the fan is being operated, the primary air flow 202 will be drawn to flow from the upstream to the downstream positions within the casing 303. The primary air flow 202 first being drawn into the apparatus through the primary air flow inlet 102, it subsequently it being adapted to pass by at least one edge of the exterior surface 402 of the main filter 303. At the time when the primary air flow 202 passes by the inner profile surface of the main filter 303, the air flow rate 204 adjacent to the inner profile surface is faster than the air flow rate 203 adjacent to the outer profile surface. Hence, the two surfaces 401 and 402 of the main filter are being exerted with different atmospheric pressures. Secondary air flow 201, which comprising the air with contaminated 201, will be entrained into the main filter through the secondary air flow inlet 103, from the surface with higher atmospheric pressure (air inlet surface of the main filter) to the surface with lower atmospheric pressure (air outlet surface of the main filter). The contaminated air is thereby being purified.

Figure 16:
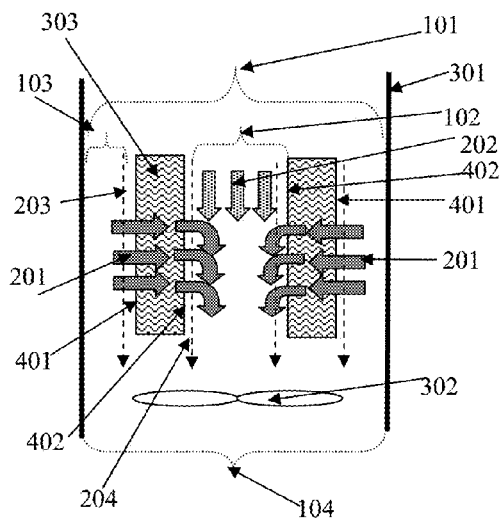
Figure 18:
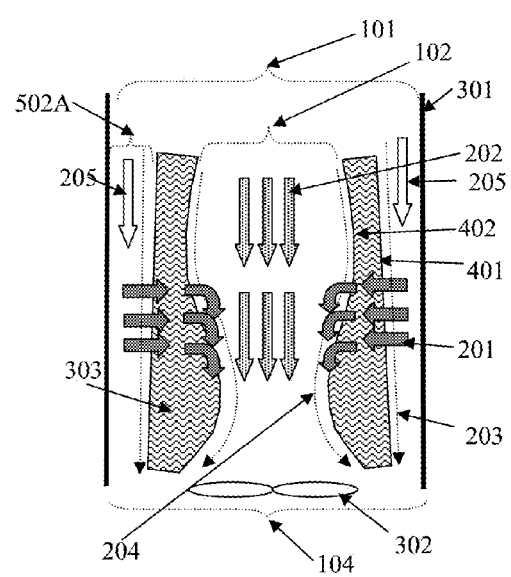

FIG. 16 and FIG. 18 indicated the embodiments of 9 and 10. The former employed the hollow cylindrical main filter which is being shown in the FIG. 8, while the latter employed the hollow cylindrical main filter which is being shown in the FIG. 9. The air purification apparatus comprising a casing 301, air inlet 101 of the apparatus, and apparatus air outlet 104, main filter 303, fan 302, the primary air flow inlet 102 and secondary air flow inlet 103. The primary air flow inlet 103 and secondary air flow inlet 103 is positioned as the air inlet 101 of the apparatus. As indicated in the figures, the primary air flow inlet 102 and the secondary air flow inlet 103 are originated from the same air inlet 101 of the apparatus. When the fan is being operated, the primary air flow 202 will be drawn to flow from the upstream to the downstream positions within the casing 303. The primary air flow 202 first being drawn into the apparatus through the primary air flow inlet 102, it subsequently it being adapted to pass by at least one edge of the exterior surface 402 of the main filter 303. At the time when the primary air flow 202 passing by the inner profile surface of the main filter 303, the air flow rate 204 adjacent to the inner profile surface is faster than the air flow rate 203 adjacent to the outer profile surface. Hence, the two surfaces 401 and 402 of the main filter are being exerted with different atmospheric pressures. Secondary air flow 201, which comprising the air with contaminated 201, will be entrained into the main filter through the secondary air flow inlet 103, from the surface with higher atmospheric pressure (air inlet surface of the main filter) to the surface with lower atmospheric pressure (air outlet surface of the main filter). The contaminated air is thereby being purified.

Figure 19:
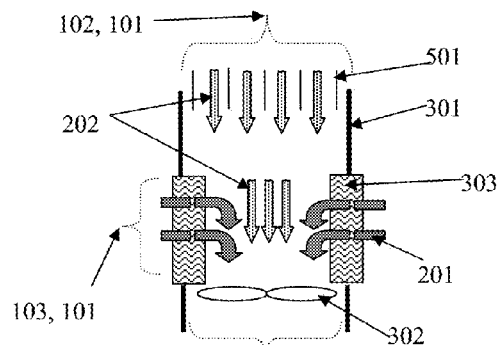
Figure 21:
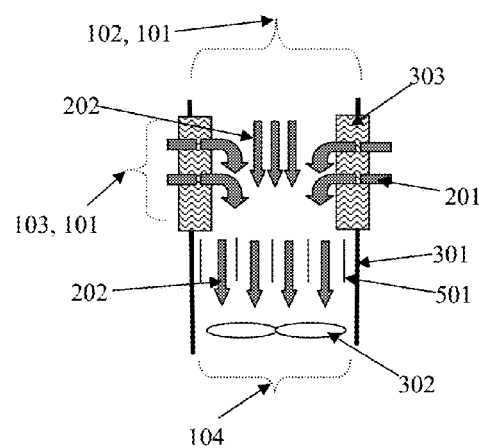

FIG. 19 and FIG. 21 indicated the embodiments of 11 and 12. As indicated in both figures, the primary air flow inlet 102 and the secondary air flow inlet 103 are originated from different air inlets 101 of the apparatus. Both embodiments employed the hollow cylindrical main filter 303 as indicated in the FIG. 8. The apparatus further comprising a auxiliary filter 501. The auxiliary filter 501 is assembled in a way that the primary air flow passes through it directly. If the auxiliary filter is being assembled at the upstream position of the main filter 303 (as shown in the embodiment 11 by FIG. 19), the contaminated air which being along with the primary air flow 202 during the operation of the fan, will first pass through the auxiliary filter 501. The contaminated air will be purified initially, and further be merged and multiplied with the purified air which is discharged by the main filter 303 at the downstream position. In the case where the auxiliary filter 501 is assembled at the downstream position of the main filter 303 (as shown in the embodiment 12 by FIG. 21), the air which purified by the main filter 303 will be merged with the primary air flow 202 at the downstream position. The multiplied air will further passes through the auxiliary filter 501. The contaminated air is therefore being doubly purified.

Figure 22:
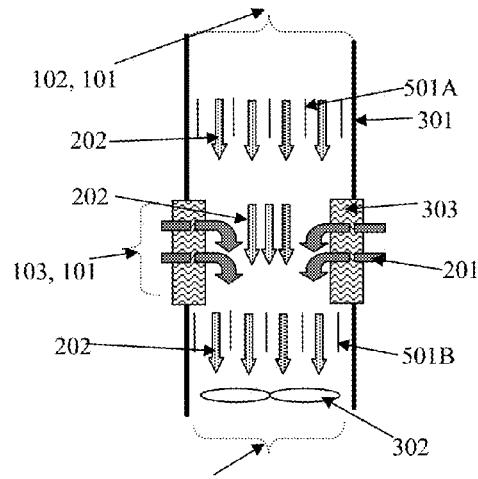

FIG. 22 indicates the embodiment 13, which the primary air flow inlet 103 and secondary air flow inlet 103 are originated from different air inlets 101 of the apparatus. The embodiment 13 comprising two auxiliary filters 501 and the hollow cylindrical main filter 303 as shown in the FIG. 8. The auxiliary filters 501 are being assembled upstream and downstream of the main filter 303.

Figure 20:
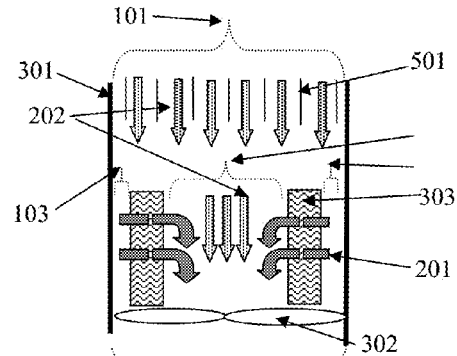
Figure 23:
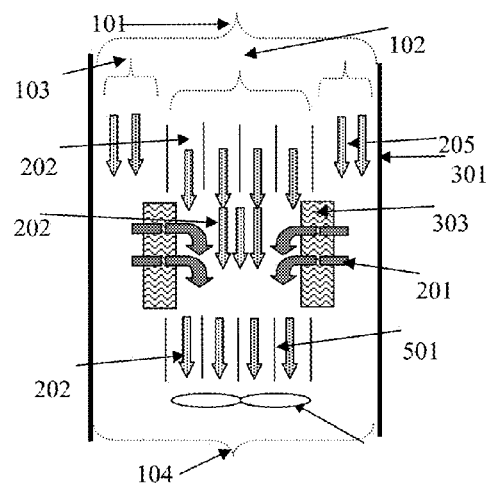
Figure 24:
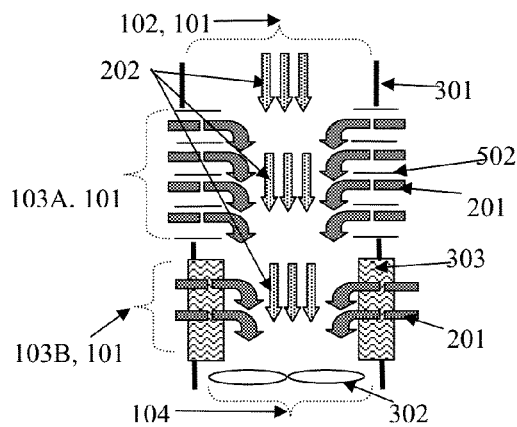
Figure 25:
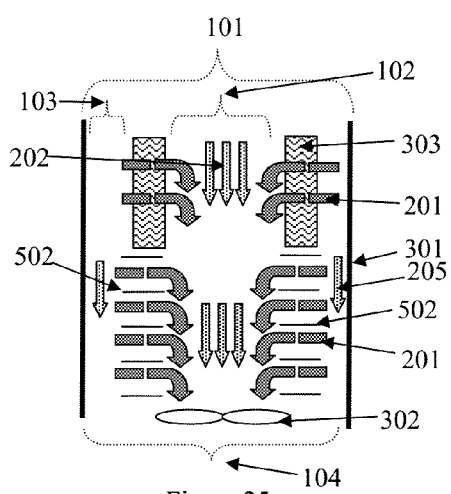
Figure 26:
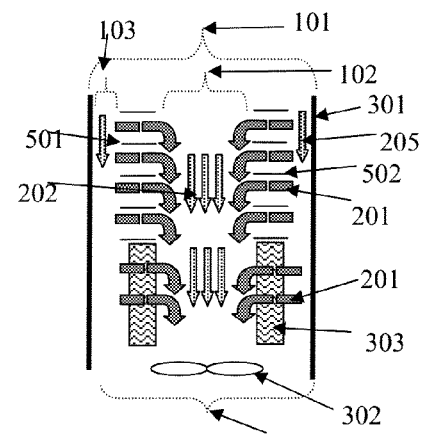
Figure 27:
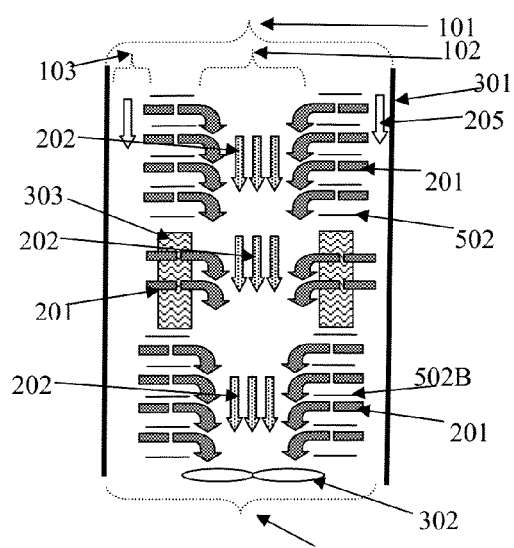
Figure 28:
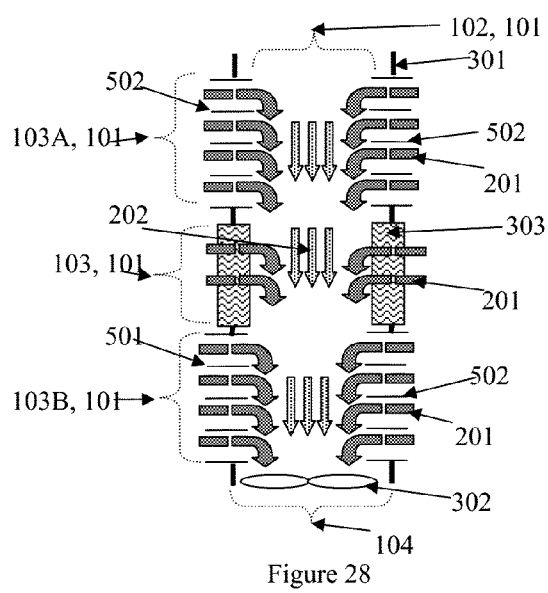
Figure 29:
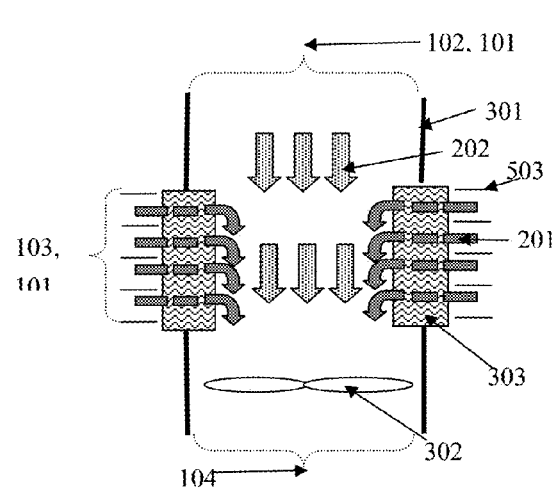
Figure 30:
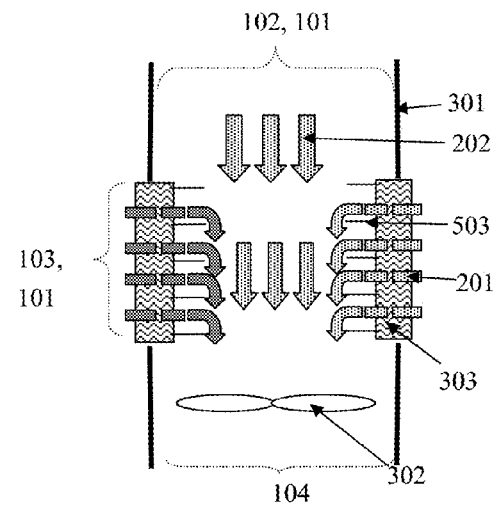
Figure 31:
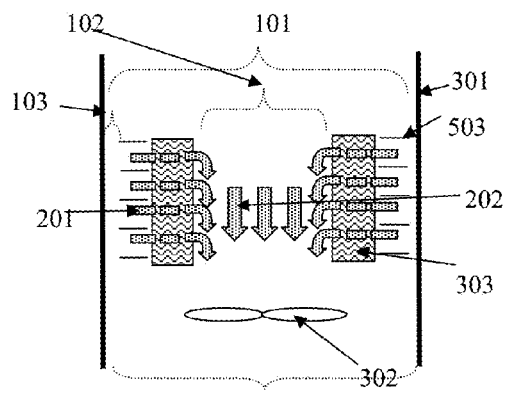
Figure 32:
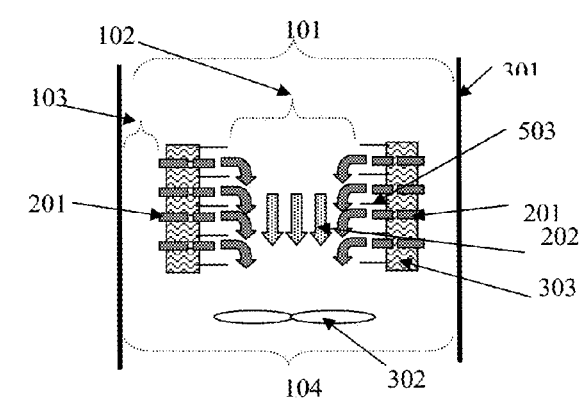
Figure 33:
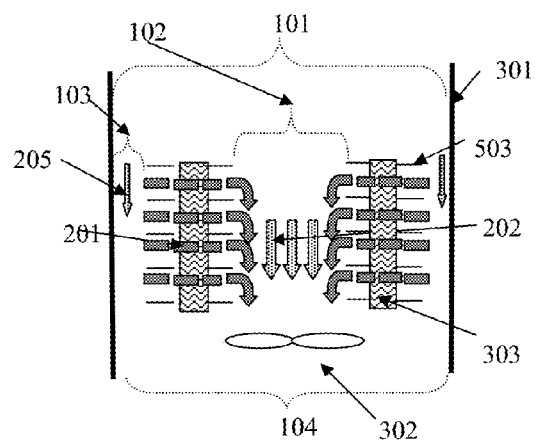
Figure 34:
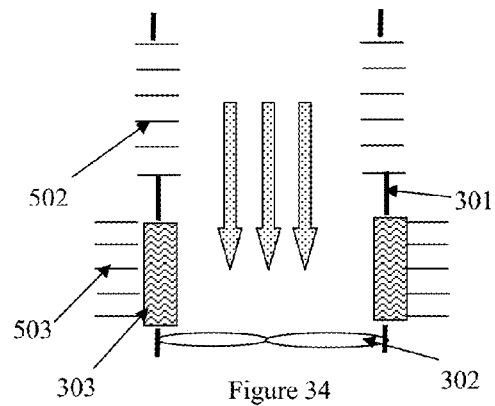
Figure 35:
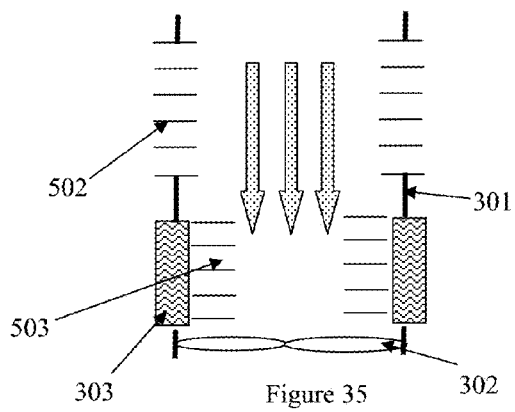
Figure 36:
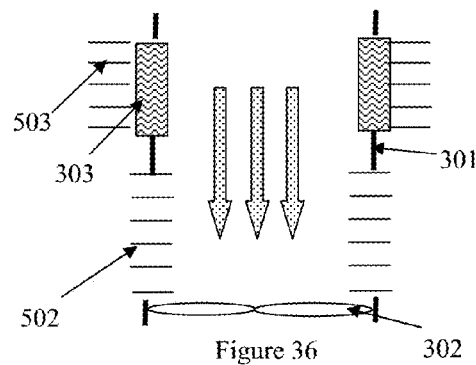
Figure 37:
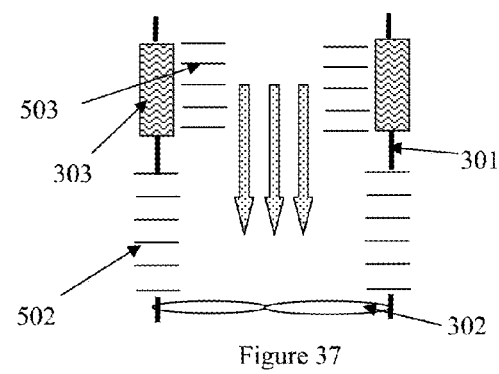
Figure 38:
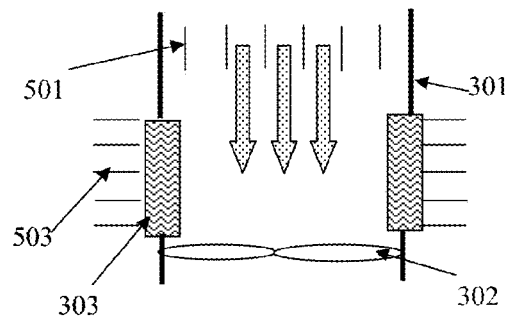
Figure 39:
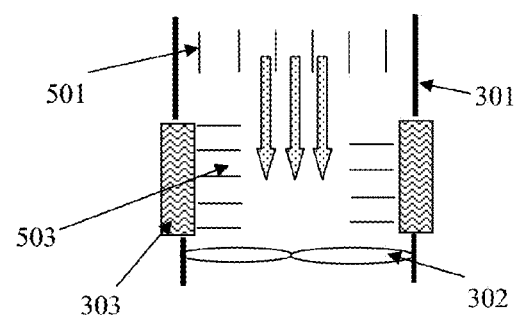
Figure 40:
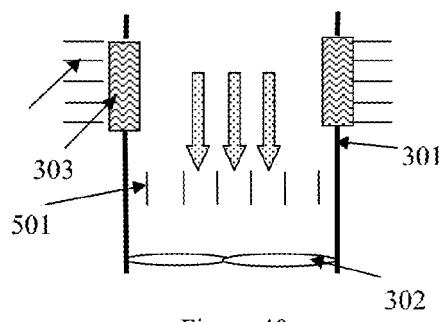
Figure 41:
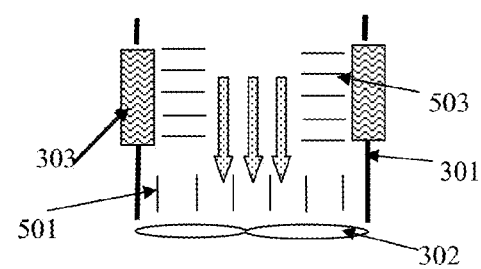
Figure 42:
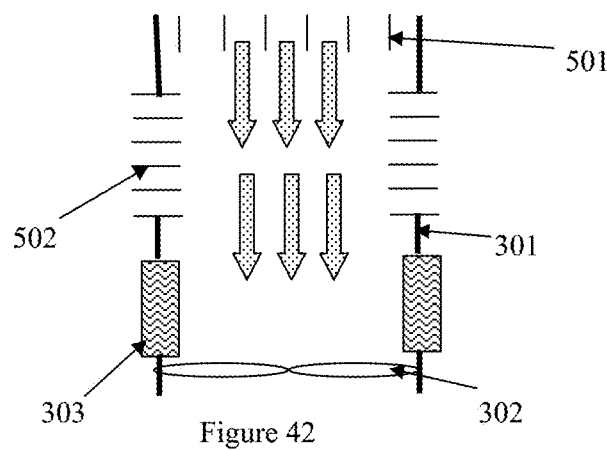
Figure 43:
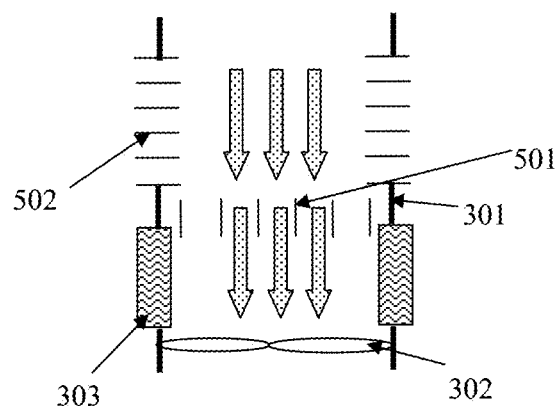
Figure 44:
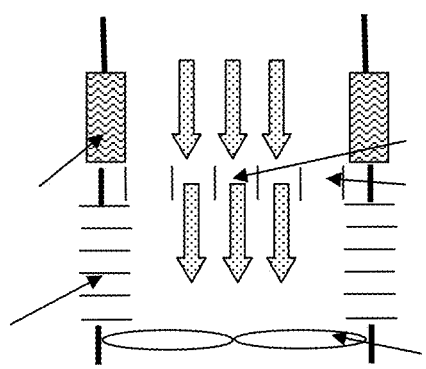
Figure 45:
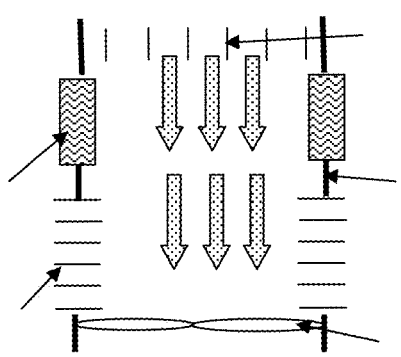

FIG. 22 and FIG. 23 indicated the embodiments of 14 and 15. As indicated in both figures, the primary air flow inlet 102 and the secondary air flow inlet 103 are originated from the same air inlets 101 of the apparatus. Both embodiments employed the hollow cylindrical main filters 303 as indicated in the FIG. 8. The apparatus further comprising an auxiliary filter 501. The auxiliary filter 501 is assembled in a way that the primary air flow pass through it directly. If the auxiliary filter is being assembled at the upstream position of the main filter 303 (as shown in the embodiment 14 by FIG. 20), the contaminated air which being along with the primary air flow 202 during the operation of the fan, will first pass through the auxiliary filter 501. The contaminated air will be purified initially, and further be merged and multiplied with the purified air which is discharged by the main filter 303 at the downstream position. In the case where the auxiliary filters 501 are assembled at the upstream and downstream position of the main filter 303 (as shown in the embodiment 15 by FIG. 23), the air which purified by the main filter 303 and the air which have been initially purified by the upstream auxiliary filter, will be merged and multiplied with the primary air flow 202 at the downstream position, the multiplied air will further passes through the auxiliary filter 501. The contaminated air is therefore being triply purified.

FIGS. 24, 25, 26, 27 and 28 indicated the embodiments of 16, 16, 18, 19 and 20 respectively. The five embodiments employed the hollow cylindrical main filters 303 as indicated in the FIG. 8. The apparatus further comprising auxiliary filter(s) 502. The auxiliary filter(s) is being assembled at the upstream position of the main filter 303 (as shown in the embodiments 16 and 18 by FIGS. 24 and 26), or downstream of the main filter 303 (as shown in the embodiment 17 by FIG. 25), or both upstream and downstream positions (as shown in the embodiments 19 and 20 by FIGS. 27 and 28). The auxiliary filter(s) are arranged in series to the main filter 303. The primary air flow inlet 102, and the secondary air flow inlet 103 and the air inlets 101 of the apparatus bearing two of the characteristics:
(1) As indicated in the embodiments 17, 18 and 19 by the FIGS. 25, 26, and 27, the primary air flow inlet 102 and the secondary air flow inlet 103 originated from the same air inlet 101 of the apparatus;
(2) As indicated in the embodiments 16 and 20 by the FIGS. 24 and 28, the primary air flow inlet 102 and the secondary air flow inlet 103 originated from the different air inlets 101 of the apparatus.

When the primary air flow being drawn by the fan 302 passes by the edge of the auxiliary filter 502, the two surfaces of the auxiliary filter are being exerted with different atmospheric pressure. The contaminated air will flow from the surface with higher atmospheric pressure to the surface with lower atmospheric pressure across the auxiliary filter 502. The contaminated air is thereby being purified. The air being purified by the auxiliary filter will be combined with the air being purified by the main filter 303.

FIGS. 29, 30, 31, 32 and 33 indicated the embodiments of 21, 22, 23, 24 and 25 respectively. The five embodiments employed the hollow cylindrical main filters 303 as indicated in the FIG. 8. The apparatus further comprising auxiliary filter(s) 503. The auxiliary filter(s) is being assembled in orientations shown below:
(1) As indicated in the embodiments 21 and 23 by the FIGS. 29 and 31, the auxiliary filter 503 being placed in front of the air inlet surface of the main filter, and arranged in parallel with the main filter.
(2) As indicated in the embodiments 22 and 24 by the FIGS. 30 and 32, the auxiliary filter 503 being placed after of the air outlet surface of the main filter, and arranged in parallel with the main filter.
(3) As indicated in the embodiment 25 by the FIG. 33, the auxiliary filters 503 being placed before and after of the air inlet and air outlet surfaces of the main filter, they are arranged in parallel with the main filter.

The five embodiments shown the following two characteristics:
(1) As indicated in the embodiments 23, 24 and 25 by the FIGS. 31, 32, and 33, the primary air flow inlet 103 and the secondary air flow inlet 103 originated from the same air inlet 101 of the apparatus; or
(2) As indicated in the embodiments 22 and 23 by the FIGS. 29 and 30, the primary air flow inlet 103 and the secondary air flow inlet 103 originated from different air inlets 101 of the apparatus.

FIGS. 34, 35, 36 and 37 indicated the embodiments of 26, 27, 28 and 29 respectively. The four embodiments employed the hollow cylindrical main filters 303 as indicated in the FIG. 8. The apparatus further comprising the auxiliary filters 502 and 503, wherein the auxiliary filter 503 and the main filter 303 are in parallel orientation. The auxiliary filter 503 is being assembled in the air inlet surface of the main filter 303 (as shown in the embodiments 25 and 28 by the FIGS. 34 and 36) or at the air outlet surface of the main filter 303 (as shown in the embodiments 27 and 29 by the FIGS. 35 and 37); another auxiliary filter 502 is being arranged in series with the main filter 303. The auxiliary filter 502 may be placed at the upstream position of the main filter 303 (as shown in the embodiments 26 and 27 by the FIGS. 34 and 35) or at the downstream position of the main filter 303 (as shown in the embodiments 28 and 29 by the FIGS. 36 and 37). When the fan is operated, the primary air is flowed from the upstream to the downstream positions, it passes by:
(1) The auxiliary filter 503, which is in parallel to the main filter; and
(2) The auxiliary filter 502 and main filter, which are arranged in series manner.

Both purified air further be merged and multiplied together before being discharged. The contaminated air are being purified.

FIGS. 38, 39, 40 and 41 indicated the embodiments of 30, 31, 32 and 33 respectively. The four embodiments employed the hollow cylindrical main filters 303 as indicated in the FIG. 8. The apparatus further comprising the auxiliary filters 501 and 503, wherein the auxiliary filter 503 and the main filter 303 are in parallel orientation. The auxiliary filter 503 is being assembled in the air inlet surface of the main filter 303 (as shown in the embodiments 30 and 32 by the FIGS. 38 and 40) or at the air outlet surface of the main filter 303 (as shown in the embodiments 31 and 33 by the FIGS. 38 and 39); another auxiliary filter 501 is being arranged in an orientation that it is being passed through by the primary air flow. The auxiliary filter 501 is being arranged at the upstream position (as shown in the embodiments 30 and 31 by the FIGS. 38 and 39) or at the downstream position (as shown in the embodiments 32 and 33 by the FIGS. 40 and 41) of the main filter 303.

Figure 46:
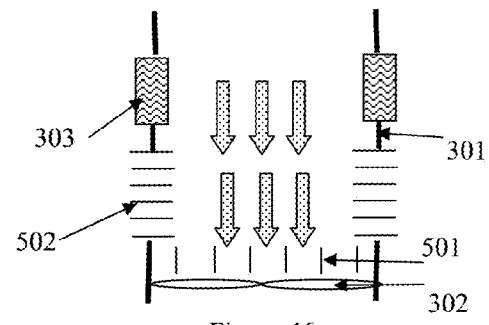
Figure 47:
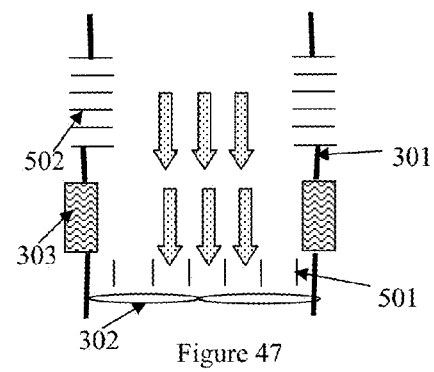
Figure 48:
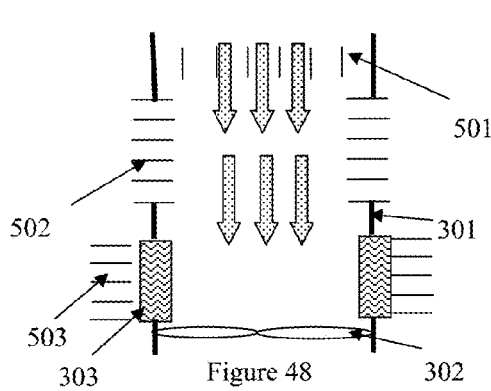
Figure 49:
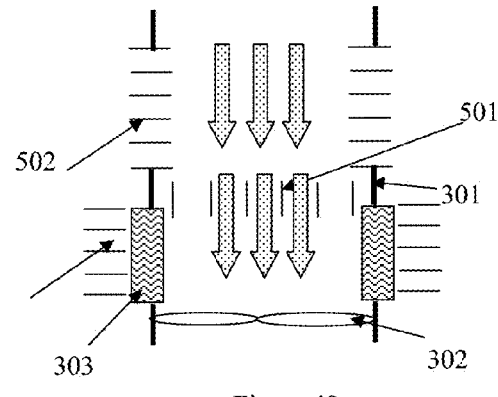

FIGS. 42, 43, 44, 45, 45 and 47 indicated the embodiments of 34, 35, 36, 37, 38 and 39 respectively. The six embodiments employed the hollow cylindrical main filters 303 as indicated in the FIG. 8. The apparatus further comprising the auxiliary filters 501 and 502, wherein auxiliary filter 501 is being arranged in an orientation that it is being passed through by the primary air flow. The auxiliary filter 501 is being placed in between the main filter 303 and auxiliary filter 502 (as indicated in the embodiments 35 and 36 by the FIGS. 43 and 44), or it is being placed upstream (as indicated in the embodiments 34 and 37 by the FIGS. 42 and 45) or downstream (as indicated in the embodiments 38 and 39 by the FIGS. 46 and 47) of the main filter 303 and the auxiliary filter 502. Another auxiliary filter 502 being placed in series with the main filter 303. The auxiliary filter 502 is being assembled in the upstream position (as indicated in the embodiments 34, 35 and 39 by the FIGS. 42, 43 and 47) or downstream position (as indicated in the embodiments 36, 37 and 38 by the FIGS. 44, 45 and 46) of the main filter 303.

FIGS. 48, 49, 50, 51, 52 and 53 indicated the embodiments of 40, 41, 42, 43, 44 and 45 respectively. The six embodiments employed the hollow cylindrical main filters 303 as indicated in the FIG. 8. The apparatus further comprising the auxiliary filters 501, 502 and 503, wherein auxiliary filter 501 is being arranged in an orientation that it is being passed through by the primary air flow. The auxiliary filter 501 is being placed in between the main filter 303 and auxiliary filter 502 (as indicated in the embodiments 41 and 42 by the FIGS. 49 and 50), or it is being placed upstream (as indicated in the embodiments 40 and 43 by the FIGS. 48 and 51) or downstream (as indicated in the embodiments 44 and 45 by the FIGS. 52 and 53) of the main filter 303 and the auxiliary filter 502. Another auxiliary filter 502 being placed in series with the main filter 303. The auxiliary filter 502 is being assembled in the upstream position (as indicated in the embodiments 40, 41 and 45 by the FIGS. 48, 49, 53) or in the downstream position (as indicated in the embodiments 42, 43 and 44 by the FIGS. 50, 51 and 52) of the main filter 303.

FIG. 54 indicates the embodiment 46, different auxiliary filters may be further co-ordinate and be assembled together and form one foremost auxiliary filter 504.

The foremost auxiliary filter 504 have one or more than one of the following characteristics:

Partial or whole of the foremost auxiliary filter being arranged in parallel with the main filter;

Partial or whole of the foremost auxiliary filter being arranged in series with the main filter;

Partial or whole of the foremost auxiliary filter being arranged in such a way that that being passed through by the primary air flow 202, which is generated and is drawn to flow from the upstream to the downstream positions by the operation of the fan 302.

There are more embodiments for the present invention. In any case, the positions of the air inlet of the apparatus, the air outlet of the apparatus, the main filter, the fan and the various positions of the auxiliary filter(s) may be arbitrary modified. Whenever it is the case that the secondary air flow, which is formed because of the different atmospheric pressures being exerted at the two exterior surfaces of the main filter; and this is the secondary air flow to entrain through the main filter; but not the primary air flow which is formed due to the operation of the fan to pass through the main filter; it will fall into the spirit of the present invention.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. An air purification apparatus, comprising:
a casing having a first air inlet devoid of a filter and a second air inlet;
a main filter disposed in the second air inlet; and
at least one means for drawing air into the casing, an air flow from a space external to the casing through the first air inlet into the casing being established to define an air flow of unfiltered air as a primary air flow and a secondary air flow being established from external the casing through the main filter into the casing, the secondary air flow being thereby filtered to remove pollutants therefrom and being combined with the primary air flow within the casing.

2. The air purification apparatus according to claim 1, further comprising at least one auxiliary filter;
the at least one auxiliary filter being positioned in the casing for filtering a second secondary air flow passing therethrough.

3. The air purification apparatus according to claim 1, wherein the air purified by the main filter and merged with the primary air flow additionally passes through the at least one auxiliary filter downstream of the second inlet.

4. The air purification apparatus according to claim 1, comprising at least one exhaust port on the casing for venting air from an internal space.

5. The air purification apparatus according to claim 1, wherein the means for drawing the primary air flow an air displacement device.

6. The air purification apparatus according to claim 1, wherein the at least one means for drawing the primary air flow is disposed in an environment device and coupled in fluid communication with the internal space of the casing.

7. The air purification apparatus according to claim 2, wherein the main filter and the at least one auxiliary filter possess different attributes, the main filter and the at least one auxiliary filter are operated at their own respective ideal air flow rates to remove different types of pollutants under one primary air flow rate in the air purification apparatus.

8. The air purification apparatus according to claim 1, wherein the main filter is a filter having a non-uniform thickness defined by an air inlet surface profile and an air outlet surface profile of the main filter having different contours.

9. The air purification apparatus according to claim 1, wherein the main filter is in the shape of a hollow cylinder with an inner surface area and an outer surface area the primary air flow only passing by the inner surface area of the main filter.

10. The air purification apparatus according to claim 1, wherein the air purification apparatus further operates in coordination with an environmental device, wherein the environmental device is one of a heater, a cooler, an air conditioner, a humidifier, a dehumidifier, a kitchen exhaust hood, a hand dryer, a food decomposer, a compost machine, a pet house or a shoe cabinet.

11. The air purification apparatus according to claim 1, further comprising at least one auxiliary filter arranged in parallel with the main filter, the at least one auxiliary filter passing a further secondary air flow therethrough.

12. The air purification apparatus according to claim 1, further comprising at least one auxiliary filter arranged in series with the main filter, the at least one auxiliary filter passing the secondary air flow therethrough.

13. The air purification apparatus according to claim 11, wherein the further secondary air flow is merged with the primary air flow within the internal space.

14. The air purification apparatus according to claim 1, wherein the main filter is in the shape of a hollow cylinder with an inner surface area and an outer surface area, the primary air flow only passing by the outer surface area of the main filter.

* * * * *